(12) United States Patent
Milos et al.

(10) Patent No.: US 8,962,286 B2
(45) Date of Patent: Feb. 24, 2015

(54) FERMENTATION PROCESSES AND BY-PRODUCTS

(75) Inventors: Klaudija Milos, Nattermannallee (DE);
Steffen Köhler, Nattermannallee (DE);
Christian Elend, Nattermannallee (DE);
Léonie Degener, Nattermannalee (DE)

(73) Assignee: Direvo Industrial Biotechnology GmbH, Cologne (DE)

( * ) Notice: Subject to any disclaimer, the term of this patent is extended or adjusted under 35 U.S.C. 154(b) by 0 days.

(21) Appl. No.: 13/995,079

(22) PCT Filed: Dec. 21, 2011

(86) PCT No.: PCT/EP2011/006473
§ 371 (c)(1),
(2), (4) Date: Aug. 19, 2013

(87) PCT Pub. No.: WO2012/084225
PCT Pub. Date: Jun. 28, 2012

(65) Prior Publication Data
US 2013/0330791 A1 Dec. 12, 2013

Related U.S. Application Data

(60) Provisional application No. 61/425,893, filed on Dec. 22, 2010.

(51) Int. Cl.
| | | |
|---|---|---|
| *A23K 1/06* | (2006.01) | |
| *C12P 7/14* | (2006.01) | |
| *C12N 9/14* | (2006.01) | |
| *C12P 7/06* | (2006.01) | |
| *C12F 3/10* | (2006.01) | |
| *A23K 1/18* | (2006.01) | |

(52) U.S. Cl.
CPC ... *C12P 7/14* (2013.01); *A23K 1/06* (2013.01); *A23K 1/1826* (2013.01); *A23K 1/184* (2013.01); *C12F 3/10* (2013.01); *C12N 9/14* (2013.01); *C12P 7/06* (2013.01); *Y02E 50/17* (2013.01)
USPC ........... 435/136; 435/157; 435/158; 435/160; 435/162; 435/168

(58) Field of Classification Search
None
See application file for complete search history.

(56) References Cited

U.S. PATENT DOCUMENTS

| | | | |
|---|---|---|---|
| 2003/0232109 A1 | 12/2003 | Dawley et al. | |
| 2006/0233864 A1* | 10/2006 | Power | 424/442 |

FOREIGN PATENT DOCUMENTS

| | | | | |
|---|---|---|---|---|
| WO | 0238786 A1 | | 5/2002 | |
| WO | WO 02038786 | * | 5/2002 | ............... C12P 7/06 |
| WO | WO 02/074895 | * | 9/2002 | |
| WO | 2004087889 A1 | | 10/2004 | |
| WO | 2007056321 A1 | | 5/2007 | |
| WO | 2009079183 A1 | | 6/2009 | |

OTHER PUBLICATIONS

Wang et al., "Effects of single or carbohydrases cocktail in low-nutrient-density diets on growth performance, nutrient digestibility, blood characteristics, and carcass traits in growing-finishing pigs" Livestock Science 126 (2009) 215-220.

* cited by examiner

*Primary Examiner* — Suzanne M Noakes
*Assistant Examiner* — Gerard Lacourciere
(74) *Attorney, Agent, or Firm* — Wagenknecht IP Law Group PC

(57) ABSTRACT

The present disclosure relates to an improved process of producing a fermentation product, in particular ethanol. The present disclosure relates also to the use of enzymes for improving the quality of by-products in the fermentative production process and to compositions comprising enzymes capable of degrading components in the fermented mash in the fermentation process.

30 Claims, 13 Drawing Sheets

FERMENTATION PROCESSES AND BY-PRODUCTS

FIELD OF THE INVENTION

The present disclosure relates to an improved process of producing a fermentation product, in particular ethanol. The present disclosure relates also to the use of enzymes for improving the quality of by-products in the fermentative production process and to compositions comprising enzymes capable of degrading components in the fermented mash in the fermentation process.

BACKGROUND OF THE INVENTION

Fermentation products, such as ethanol, are produced by first degrading starch-containing material into fermentable sugars by liquefaction and saccharification and then converting the sugars directly or indirectly into the desired fermentation product using a fermenting organism. Liquid fermentation products such as ethanol are recovered from the fermented mash (often referred to as "beer" or "beer mash"), e.g., by distillation, which separate the desired fermentation product from other liquids and/or solids. The remaining faction, referred to as "whole stillage", is dewatered and separated into a solid and a liquid phase, e.g., by centrifugation. The solid phase is referred to as "wet cake" (or "wet grains" or "WDG") and the liquid phase (supernatant) is referred to as "thin stillage". Dewatered wet cake is dried to provide "Distillers Dried Grains" (DDG) used as nutrient in animal feed. Thin stillage is typically evaporated to provide condensate and syrup (or "thick stillage") or may alternatively be recycled directly to the slurry tank as "backset". Condensate may either be forwarded to a methanator before being discharged or may be recycled to the slurry tank. The syrup consisting mainly of limit dextrins and non-fermentable sugars may be blended into DDG or added to the wet cake before drying to produce DDGS (Distillers Dried Grain with Solubles).

It is known to commercially use the various byproducts and residues derived from the fermentation processes like the ethanol production process. Distillers residues or byproducts, as well as by-products of cereal and other food industry manufacturing, are known to have a certain value as sources of protein and energy for animal feed. Furthermore, the oil from the by-products like DDGS can be recovered as a separate by-product for use in biodiesel production or other biorenewable products are sought.

The by-products like DDG, DDGS or WDG comprises proteins, fibers, fat and unconverted starch. For example DDGS contains typically about 30% of protein. While the protein content is high the amino acid composition is not well suited for monogastric animals if used as animal feed. In general processing of DDGS, especially drying time and temperature are effecting the availability and digestibility of the amino acids, especially lysine.

Furthermore, the by-products are mainly fibrous by-products comprising Crude Fibers (CF), which are structural carbohydrates consisting of cellulose, hemicellulose and indigestible materials like lignin. The structural carbohydrates are not digestible in animal's small intestine. Fibers are characterized and analyzed by different methods and can be divided into crude fibers (CF), neutral detergent fibers (NDF) and acid detergent fibers (ADF). The proportion of cellulose and lignin in the crude fibers fraction also determines the digestibility of crude fibers or its solubility in the intestine. High cellulose and lignin concentrations mean reduced digestibility and vice versa. Hemicelluloses are capable to bind water. The soluble part of fibres the soluble non-starch-polysaccharides (NSP) cannot be digested by monogastric animals like swine and poultry, but increase viscosity, due to their capability to bind water, and are a nutritional constraint, since they can cause moist, sticky droppings and wet litter. The antinutritional effect of soluble NSP's is mainly related to the increase in digesta viscosity. The increased viscosity is slowing down the feed passage rate and hinders the intestinal uptake of nutrients and can lead to decreased feed uptake The viscosity increase a) hinders the intestinal absorption of nutrients and can result in negative effect on the consistency on faces and even symptoms of diarrhea, b) slowing down the feed passage rate and possibly to decreased feed intake. Another effect of NSP's is the so-called "Nutrient Encapsulation". The NSP's in plant cell wall encapsulated starch, protein, oil and other nutrients within the plant cell which is an impermeable barrier preventing full utilization of the nutrients within the cell.

Furthermore the soluble NSP's are responsible for high viscosities during fermentation and are directly influencing separation and drying conditions of fermentation by-products like DDGS in the production process. The bound or encapsulated water in the product is difficult to remove and causes the use of higher drying temperatures and also longer drying time, adversely affecting the quality of temperature-sensitive products like amino acids. The availability and digestibility of essential amino acids in the by-products are lowered by high temperatures and long drying time during production. Examples for NSPs are arabinoxylans, beta-glucans, galactomannans and alpha-galactosides.

As the by-products are used in animal feed for monogastrics animals like pigs and poultry it is important that the by-products have high concentrations of protein with a good amino acid composition and high availability and low soluble fibers content.

Therefore, the two ways for an improvement of a fermentative production plant ton increase their efficiency and profitability are an improved production process and the improvement of the quality of the by-products.

In the prior art, a lot of specific processes or treatment methods are described to improve fermentative production processes.

For example, WO 2007/056321 A1 discloses a method of dewatering whole stillage comprising adding enzymes to whole stillage in the ethanol production to improve the solid-liquid separation in the process.

WO 02/38786 describes a process of ethanol production, whereby enzymes are used for thinning the liquefied whole grain mash and the thin stillage. Enzymes are applied to the liquefied mash before the fermentation starts as well as to the thin stillage after centrifugation of the whole stillage.

The US 2006/0275882 A1 describes a process for producing a fermentation product wherein the viscosity of the mash is reduced by the application of enzymes before or during the fermentation.

The US 2006/0233864 A1 describes a method for improving the nutritional quality of fibrous by-products for a food manufacturing process, wherein the fibrous by-products like DDGS are inoculated with a filamentous fungus to improve the quality of the by-product.

Some ethanol plants use milo, wheat, or barley in the fermentation process, depending on geographical location and time of the year. As a result, nutrient composition can vary among DDGS sources. Because of the near complete fermentation of starch, the remaining amino acids, fat, minerals and vitamins increase approximately three-fold in concentration compared to levels found in corn. Despite the significant increase in crude protein, the poor amino acid balance of DDGS must be addressed when formulating swine and poultry diets.

Therefore, it is an object of the present disclosure to provide improved methods for improving the quality of the by-products from fermentation processes. It is further a need for methods for further improvement of the process ability by dewatering the stillage and to provide improved methods for increasing the amount of recoverable oil.

SUMMARY OF THE DISCLOSURE

The present disclosure relates to methods for the improvement of the quality of the by-products or residues derived from fermented mash comprising the steps of: i) subjecting the fermented mash during or after the fermentation to an enzyme composition comprising an enzyme or a mixture of enzymes capable of degrading one or more fermented mash components, ii) separating the desired fermentation product.

The present disclosure also relates to methods of producing ethanol from starch containing material, said method comprising the steps of:
  i) Converting starch containing material to fermentable sugars
  ii) Fermentation of the fermentable sugars with a microorganism to fermented mash
  iii) Subjecting the fermented mash after the fermentation process to an enzyme composition comprising an enzyme or a mixture of enzymes
  iv) Separation of the ethanol in the fermented mash by distillation The present disclosure also relates to uses of an enzyme composition comprising a beta-1,3-glucanase and/or a xylanase for the improvement of the nutritional quality of the by-products or residues derived from fermented mash in a fermentative production process.

The present disclosure relates to a process of fermenting a starch-containing material into a fermentation product comprising a fermentation step without the presence of a beta 1,3-glucanase and/or a xylanase. After the fermentation an enzyme composition is added to the fermented mash for an improvement of the by-products like the fibrous by-products such as spent brewer's grains, dried distiller's grains, dried distiller's soluble, distiller's dried grains with soluble, wet grains, and mixtures thereof.

DESCRIPTION OF THE INVENTION

Figure 1:
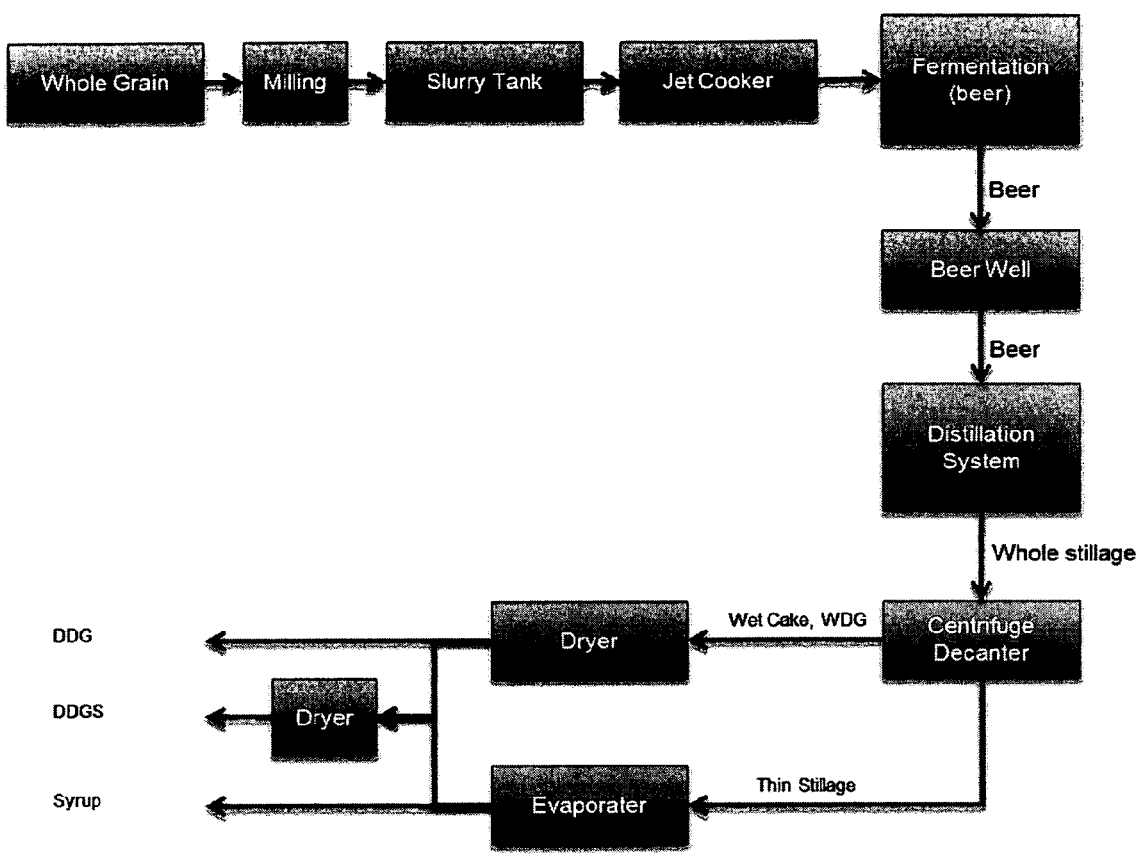
FIG. 1 schematically shows an ethanol production process.

The object of the present invention is to provide improved fermentative production processes due to a better process ability and to provide by-products from the fermentation process with an improved quality.

One aspect of the present disclosure relates to methods for improving the quality of by-products or residues derived from starch-containing material in a processes for producing fermentation products comprising the steps of: i) subjecting the fermented mash after the fermentation to an enzyme composition comprising an enzyme or a mixture of enzymes capable of degrading one or more fermented mash components, ii) separating the desired fermentation product.

By-products or residues of the fermenting process includes distillers' grain, brewer's grains, dried distiller's grains, dried distiller's solubles, distiller's dried grains with solubles, WDG or/and residues of the cereal processing industry, or mixtures thereof. For example, DDGS are the dried residue remaining after the starch fraction of corn is fermented with selected yeasts and enzymes to produce ethanol and carbon dioxide. After complete fermentation, the alcohol is removed by distillation and the remaining fermentation residues are dried.

Stillage is the product which remains after the mash has been converted to sugar, fermented and distilled into ethanol. Stillage can be separated into two fractions, such as, by centrifugation or screening: (1) wet cake (solid phase) and (2) the thin stillage (supernatant). The solid fraction or distillers' wet grain (DWG) can be pressed to remove excess moisture and then dried to produce distillers' dried grains (DDG). After ethanol has been removed from the liquid fraction, the remaining liquid can be evaporated to concentrate the soluble material into condensed distillers' solubles (DS) or dried and ground to create distillers' dried solubles (DDS). DDS is often mixed with DDG to form distillers' dried grain with solubles (DDGS). DDG, DDGS, and DWG are collectively referred to as distillers' grain(s).

In one embodiment of the present disclosure enzymes were added during and/or preferably after the fermentation in the production process to the fermented mash and before the separation step like distillation, where the desired fermentation main product is separated from the rest of the fermented mash. The enzymes according to the present disclosure were capable of degrading components in the fermented mash (beer or beer mash) which improves the quality of by-products or residues like brewer's grains, dried distiller's grains, dried distiller's solubles, distiller's dried grains with solubles, WDG or/and residues of the cereal processing industry, or mixtures thereof. Components of the fermented mash can be cell walls, cell-walls of fermenting microorganisms, microorganisms, fibers etc.

Surprisingly, the degradation of the fermenting microorganisms itself by adding the enzyme composition according to the present disclosure, in particular by using the beta 1,3 glucanase and/or the beta 1,6 glucanase, particularly in combination with a xylanase and/or a mannanase, results in an increase of the nutrition content in the beer mash which results in an improvement of the nutrition quality like the protein content of the byproducts, as well as reduction of NSPs resulting from the fermentative organism cell wall like the yeast cell wall.

Therefore, in advantageous embodiments, the enzyme compositions used in the methods according to the present disclosure are capable to degrade the cell wall components of the fermenting organisms after the fermentation step as well as the fibers in the beer.

In one aspect of the present disclosure, the quality of byproducts from a fermentative production process like DDG, DDGS or WDG can be improved with the methods according to the present disclosure by reducing the fiber content of the by-products.

Another aspect of the present disclosure is a better dewatering of the whole stillage from the fermentative production process to improve the drying conditions of the by-products.

Yet another aspect of the present disclosure is the improved evaporation of water from the thin stillage to improve the production and composition of the thick stillage or syrup.

In another aspect of the present disclosure, the amount of recoverable oil is increased. DDGS following an ethanol production process from corn typically contains about 13% oil, 31% protein and 56% carbohydrates and other components. Removal of some of the oil from the DDGS will improve the quality of the DDGS for the feed market as many feed producers prefer less oil and fat in the DDGS to make high quality feed.

The method of the invention may be used on beer derived from production of any suitable fermentation product. The feedstock for producing the fermentation product may be any starch- and/or sugar containing material, preferably starch- and/or sugar containing plant material, including: sugar cane, tubers, roots, whole grain; and any combination thereof.

The starch-containing material may be obtained from cereals. Suitable starch-containing material includes corn (maize), wheat, barley, cassava, sorghum, rye, triticale, potato, or any combination Corn is the preferred feedstock, especially when the fermentation product is ethanol. The starch-containing material may also consist of or comprise, e.g., a side stream from starch processing, e.g., C6 carbohydrate containing process streams that may not be suited for production of syrups. Beer components include fiber, hull, germ, oil and protein components from the starch-containing feedstock as well as non-fermented starch, yeasts, yeast cell walls and residuals. Production of a fermentation product is typically divided into the following main process stages: a) Reducing the particle size of starch-containing material, e.g., by dry or wet milling; b) Cooking the starch-containing material in aqueous slurry to gelatinize the starch, c) Liquefying the gelatinized starch-containing material in order to break down the starch (by hydrolysis) into maltodextrins (dextrins); d) Saccharifying the maltodextrins (dextrins) to produce low molecular sugars (e.g., DPI-2) that can be metabolized by a fermenting organism; e) Fermenting the saccharified material using a suitable fermenting organism directly or indirectly converting low molecular sugars into the desired fermentation product; f) Recovering the fermentation product, e.g., by distillation in order to separate the fermentation product from the fermentation mash.

As mentioned above beer (or fermented mash) is the fermentation product consisting of ethanol, other liquids and solids of a desired fermentation product. According to the invention the fermentation product may be any fermentation product, including alcohols (e.g., ethanol, methanol, butanol, 1,3-propanediol); organic acids (e.g., citric acid, acetic acid, itaconic acid, lactic acid, gluconic acid, gluconate, succinic acid, 2,5-diketo-D-gluconic acid); ketones (e.g., acetone); amino acids (e.g., glutamic acid); gases (e.g., $H_2$ and $CO_2$), and more complex compounds, including, for example, antibiotics (e.g., penicillin and tetracycline); enzymes; vitamins (e.g., riboflavin, B12, beta-carotene); and hormones. Fermentation is also commonly used in the production of consumable alcohol (e.g., spirits, beer and wine), dairy (e.g., in the production of yogurt and cheese), leather, and tobacco industries. In a preferred embodiment the fermentation product is a liquid, preferably an alcohol, especially ethanol. The beer contemplated according to the invention may be the product resulting from a fermentation product production process including above mentioned steps a) to f). However, the beer may also be the product resulting from other fermentation product production processes based on starch- and/or lignocellulose containing starting material.

The fermenting organism may be a fungal organism, such as yeast, or bacteria. Suitable bacteria may e.g. be *Zymomonas* species, such as *Zymomonas mobilis* and *E. coli*. Examples of filamentous fungi include strains of *Penicillium* species. Preferred organisms for ethanol production are yeasts, such as e.g. *Pichia* or *Saccharomyces*. Preferred yeasts according to the disclosure are *Saccharomyces* species, in particular *Saccharomyces cerevisiae* or baker's yeast.

In a further embodiment, the solids from the fermentation step can be fractionated. After fermentation large pieces of fibers could be removed prior or after distillation. Removal can be effected with a surface skimmer before to distillation of beer. The material can be separated from the ethanol/water mix by, e.g. centrifugation. Alternatively, fibers and germs can be removed by screening the whole stillage after distillation or the grinded grains before fermentation. After germs and large pieces of fibers are removed the remaining beer or whole stillage are treated with enzymes or enzyme combinations to further improve the nutritional quality of the final byproduct like DDGS to be used.

Based on whole stillage or WDG in one embodiment of the present disclosure an additional fermenter can be introduced for an onsite enzyme production, producing a plant and process specific enzyme mixture with filamentous fungi. The supernatant of this fermentation comprising enzymes is directly transferred into the main fermenter or beer well in order to reduce the fiber content and improve quality and nutritional factors of DDGS, WDG and/or other by products.

Furthermore, the use of the enzyme compositions according to the present disclosure in the beer mash after the fermentation and before the distillation process can reduce the viscosity of the beer mash through the degradation of fibers and/or the fermentative microorganisms in the beer. The reduction of the fibers in the beer results in a reduction of the fiber content in the by-products. The early degradation of the NSP's has a direct influence on the separation and the drying conditions of the by-products like DDGS in the production process. The lower viscosity results in lower drying temperatures and also in a shorter drying time resulting in an improved quality of the by-products. For example, the temperature sensitive products like proteins and amino acids are not destroyed.

Further, by adding the enzymes according to the present disclosure to the fermented mash before the distillation step is an advantage since the enzymes in the enzyme compositions are inactivated during the distillation.

Due to the improved quality, the by-products and residues can be used as high quality animal feed with a low fiber and oil and high protein content.

In one embodiment, the disclosure relates to methods for formulating nutritionally useful feed additives as co-products of the above-referenced methods for improving nutritional characteristics of a fibrous food product.

The processes for producing fermentation products includes the production of a large number of fermentation products comprising but not limited to alcohols (in particular ethanol); acids, such as citric acid, itaconic acid, lactic acid, gluconic acid, lysine; ketones; amino acids, such as glutamic acid, but also more complex compounds such as antibiotics, such as penicillin, tetracyclin; enzymes; vitamins, such as riboflavin, B12, beta-carotene; hormones, such as insulin. Preferred is drinkable ethanol as well as industrial and fuel ethanol.

Processes for producing fermentation products, such as ethanol, from a starch or lignocellulose containing material are well known in the art. The preparation of the starch-containing material such as corn for utilization in such fermentation processes typically begins with grinding the corn in a dry-grind or wet-milling process. Wet-milling processes involve fractionating the corn into different components where only the starch fraction enters into the fermentation process. Dry-grind processes involve grinding the corn kernels into meal and mixing the meal with water and enzymes. Generally two different kinds of dry-grind processes are used. The most commonly used process, often referred to as a "conventional process," includes grinding the starch-containing material and then liquefying gelatinized starch at a high temperature using typically a bacterial alpha-amylase, followed by simultaneous saccharification and fermentation (SSF) carried out in the presence of a glucoamylase and a fermentation organism. Another well-known process, often referred to as a "raw starch hydrolysis" process (RSH process), includes grinding the starch-containing material and then simultaneously saccharifying and fermenting granular starch below the initial gelatinization temperature typically in the presence of an acid fungal alpha-amylase and a glucoamylase.

In a process for producing ethanol from corn, following SSF or the RSH process the ethanol is distilled from the whole mash after fermentation. The resulting ethanol-free slurry, usually referred to as whole stillage, is separated into solid and liquid fractions (i.e., wet cake and thin stillage containing about 35 and 7% solids, respectively). The thin stillage is often condensed by evaporation into a thick stillage or syrup and recombined with the wet cake and further dried into distillers' dried grains with solubles distillers' dried grain with solubles (DDGS) for use in animal feed.

Enzymes used for degrading beer components include carbohydrases such as alpha-amylase, glucoamylase, cellulose and/or hemicellulases, such as mannanases, xylanases and beta-glucanases, pectinases and proteases, or a mixture thereof.

In advantageous embodiment, the enzyme compositions comprise a beta-1,3-glucanase, in particular for the degradation of the cell walls from the fermenting microorganisms. To avoid the degradation of the fermentative microorganisms the enzyme composition is added after the fermentation step. As used herein "after the fermentation" or "after the fermentation step" means that a large part or all of the fermentable sugars like glucose are converted to the desired fermentation products such as ethanol.

In an embodiment, the enzyme composition comprises a beta-1,3-glucanase and a 1,6-beta-glucanase. In another embodiment, the enzyme composition comprises a xylanase. In an advantageous embodiment, the enzyme composition comprises a beta-1,3-glucanase and a xylanase. In another embodiment, the enzyme composition comprises a beta-1,3-glucanase, a 1,6-beta-glucanase and a xylanase.

In further embodiments, the enzyme composition comprises in addition a pectinase and/or a protease. In an example the enzyme composition comprises a beta-1,3-glucanase, a xylanase and a protease. In another example the enzyme composition comprises a beta-1,3-glucanase, a xylanase and a pectinase.

In a further embodiment, enzyme composition comprises a mannanase. In an advantageous embodiment the enzyme composition comprises a mannanase and a beta-1,3-glucanase.

The cell walls of most true fungal and yeast microorganisms contain a network of glucan, which gives the cell wall strength. Further major fungal cell walls constituents are mannoprotein and chitin. For the degradation of the fermented mash components, in particular for the degradation of the fibers and the fermenting microorganisms the following enzymes may be used.

Beta-1,3-glucanases as used herein are enzymes capable of degrading of glucan. Glucan and chitin are far more resistant to microbial degradation than cellulose, which is the major constituent of the cell wall of many yeasts and fungi-like organisms. Glucan is predominantly beta-1,3-linked with some branching via 1,6-linkage (Manners et al., Biotechnol. Bioeng, 38, p. 977, 1973), and is known to be degradable by certain beta-1,3-glucanase systems. beta-1,3-glucanase includes the group of endo-beta-1,3-glucanases also called laminarinases (E.C. 3.2.1.39 and E.C. 3.2.1.6, Enzyme Nomenclature, Academic Press, Inc. 1992).

A number of beta-1,3-glucanase genes and uses thereof have been disclosed in the prior art. An example is DD 226012 (Akad. Wissenshaft, DDR) which concerns a method for production of a *Bacillus* beta-1,3-glucanase. Further, JP 61040792 A (DOI K) describes a cell wall-cytolase beta-1,3-glucanase recombinant plasmid for removing the cell walls of yeast. The gene is derived from *Arthrobacter* and is transformed in *Escherichia* group bacteria. EP 440.304 concerns plants provided with improved resistance against pathogenic fungi transformed with at least one gene encoding an intracellular chitinase, or in intra- or extracellular beta-1,3-glucanase. The matching recombinant polynucleotides is also disclosed. WO 87/01388 (The Trustees of Columbia University) describes a method for preparing cell lytic enzymes, such as beta-1,3-glucanases, which can be produced by Oerksovia. WO 92/03557 (Majesty (Her) in Right of Canada) discloses a recombinant DNA expression vector comprising a 2.7 kb DNA sequence, derived from *Oerskovia xanthineolytica*, encoding a beta-1,3-glucanase. From WO 92/16632 a recombinant DNA sequence coding for a novel protein with beta-1,3-glucanase activity, is known.

Examples for commercial available beta-1,3-glucanase are Rohalase BX from AB Enzymes and Rapidase Glucalees from DSM.

Hemicellulases as used herein are enzymes capable to break down hemicellulose. Any hemicellulase suitable for use in hydrolyzing hemicellulose, may be used. Preferred hemicellulases include acetylxylan esterases, endo-arabinases, exo-arabinases, arabinofuranosidases, feruloyl esterase, endo-galactanases, exo-galactanases, glucuronidases, mannases, xylanases, and mixtures of two or more thereof. Preferably, the hemicellulase for use in the present invention is an endo-acting hemicellulase, and more preferably, the hemicellulase is an exo-acting hemicellulase which has the ability to hydrolyze hemicellulose under acidic conditions of below pH 7, preferably pH 3-7.

In one aspect, the hemicellulase(s) comprises a commercial hemicellulolytic enzyme preparation. Examples of commercial hemicellulolytic enzyme preparations suitable for use in the present invention include, for example, SHEARZYME™ (Novozymes A/S), CELLIC™ HTec (Novozymes A/S), CELLIC™ HTec2 (Novozymes A/S), VISCOZYME™ (Novozymes A/S), ULTRAFLO® (Novozymes A/S), PULPZYME™ HC (Novozymes A/S), MULTIFECT® Xylanase (Genencor), ACCELLERASE™ XY (Genencor), ACCELLERASE™ XC (Genencor), ECOPULP™ TX-200A (AB Enzymes), HSP 6000 Xylanase (DSM), DEPOL™ 333P (Biocatalysts Limit, Wales, UK), DEPOL™ 740L. (Biocatalysts Limit, Wales, UK), and DEPOL™ 762P (Biocatalysts Limit, Wales, UK).

Preferably, the hemicellulase for use in the present disclosure is an endo-acting hemicellulase, which has the ability to hydrolyze hemicellulose under acidic conditions of below pH 7. An example of hemicellulase suitable for use in the present invention includes VISCOZYME L™ (available from Novozymes A/S, Denmark), Rohament GMP™ (available from AB Enzymes).

In an embodiment the hemicellulase is a xylanase. In an embodiment the xylanase may preferably be of microbial origin, such as of fungal origin (e.g., *Aspergillus, Fusarium, Humicola, Meripilus, Trichoderma*) or from a bacterium (e.g., *Bacillus*). In a preferred embodiment the xylanase is derived from a filamentous fungus, preferably derived from a strain of *Aspergillus*, such as *Aspergillus* aculeatus; or a strain of *Humicola*, preferably *Humicola lanuginosa*. Examples of xylanases useful in the methods of the present invention include, but are not limited to, *Aspergillus aculeatus* xylanase (GeneSeqP:AAR63790; WO 94/21785), *Aspergillus fumigatus* xylanases (WO 2006/078256), and *Thielavia terrestris* NRRL 8126 xylanases (WO 2009/079210). The xylanase may preferably be an endo-1,4-beta-xylanase, more preferably an endo-1,4-beta-xylanase of GH 10 or GH 11. Examples of commercial xylanases include SHEARZYME™, BIOFEED WHEAT™, HTec and HTec2 from Novozymes A/S, Denmark.

Examples of beta-xylosidases useful in the methods of the present invention include, but are not limited to, *Trichoderma reesei* beta-xylosidase (UniProtKB/TrEMBL accession number Q92458), *Talaromyces emersonii* (SwissProt accession number Q8X212), and *Neurospora crassa* (SwissProt accession number Q7SOW4).

According to the invention beer may in step i) be subjected to an effective amount of any xylanase (EC 3.2.1.8), such as any of below mentioned xylanases. Xylanase activity may be derived from any suitable organism, including fungal and bacterial organisms. Fungal xylanases may be derived from strains of genera including *Aspergillus, Disporotrichum, Penicillium, Neurospora, Fusarium* and *Trichoderma*.

Examples of suitable bacterial xylanases include xylanases derived from a strain of *Bacillus*, such as *Bacillus subtilis*, such as the one disclosed in U.S. Pat. No. 5,306,633.

Contemplated commercially available xylanases include SHEARZYME™, BIOFEED WHEAT™, (from Novozymes AJS), Econase CE™ (from AB Enzymes), Depol 676™ (from Biocatalysts Ltd.) and SPEZYME™ CP (from Genencor Int.).).

Xylanase may be added in an amount effective in the range from $0.16 \times 10^{<6>}-460 \times 10^{<6>}$ Units per ton beer mash.

Mannanases are hemicellulases classified as EC 3.2.1.78, and called endo-1,4-beta-mannosidase. Mannanase includes beta-mannanase, endo-1,4-mannanase, and galacto-mannanase. Mannanase is preferably capable of catalyzing the hydrolysis of 1,4-beta-D-mannosidic linkages in mannans, including glucomannans, galactomannans and galactoglucomannans. Mannans are polysaccharides primarily or entirely composed of D-mannose units. The mannanase may be of any origin such as a bacterium or a fungal organism. In a specific embodiment the mannanase is derived from a strain of the filamentous fungus genus *Trichoderma*, preferably *Trichoderma reseei*. In an embodiment the mannanase is one of the mannanases described in WO2008/009673.

Mannanases have been identified in several *Bacillus* organisms. For example, Talbot et al., Appl. Environ. Microbiol., Vol. 56, No. 11, pp. 3505-3510 (1990) describes a beta-mannanase derived from *Bacillus stearothermophilus*. Mendoza et al., World J. Microbiol. Biotech., Vol. 10, No. 5, pp. 551-555 (1994) describes a beta-mannanase derived from *Bacillus subtilis*. JP-A-03047076 discloses a beta-mannanase derived from *Bacillus* sp. JP-A-63056289 describes the production of an alkaline, thermo stable beta-mannanase. JP-A-63036775 relates to the *Bacillus* microorganism FERM P-8856 which produces beta-mannanase and beta-mannosidase. JP-A-08051975 discloses alkaline beta-mannanases from alkalophilic *Bacillus* sp. AM-001. A purified mannanase from *Bacillus amyloliquefaciens* is disclosed in WO 97/11164. WO 91/18974 describes a hemicellulase such as a glucanase, xylanase or mannanase active. Examples of commercially available mannanases include GAMANASE™ available from Novozymes A/S Denmark and Rohapect GMP™ available from AB Enzymes GmbH.

Mannanase may be added in an amount effective in the range from $0.3 \times 10^{<6>}-1.6 \times 10^{<6>}$ Units per ton beer mash.

A cellulase, used in accordance with the disclosure, may be any cellulase, in particular of microbial origin, in particular fungal or bacterial origin such as a cellulase derivable from a strain of a filamentous fungus (e.g., *Aspergillus, Trichoderma, Humicola, Fusarium*). Preferably, the cellulase acts on both cellulosic and lignocellulosic material. Preferred cellulases for use in the present invention include endo-acting cellulases, exo-acting celluases and cellobiases, and combinations thereof. Examples of commercially available cellulases suitable according to the present invention include, for example, CELLULCLAST™ (available from Novozymes A/S), LAMINEX™ and SPEZYME™ CP (Genencor Int.) and Econase CE™ (from AB Enzymes GmbH), Rohalase BX™ (from Ab Enzymes GmbH), Cellulase 13P™ (from Biocatalysts Ltd.). Cellulase may be added in amounts effective in the range or from $0.03 \times 10^{<6>}-16 \times 10^{<6>}$ Units per ton substrate (in beer mash)

The pectinase used in the methods according to the present disclosure may be any pectinase, in particular of microbial origin, in particular of bacterial origin, such as a pectinase derived from a species within the genera *Bacillus, Clostridium, Pseudomonas, Xanthomonas* and *Erwinia*, or of fungal origin, such as a pectinase derived from a species within the genera *Trichoderma* or *Aspergillus*, in particular from a strain within the species *A. niger* and *A. aculeatus*. Contemplated commercially available pectinases include Pectinex Ultra-SPL™ (from Novozymes), Pectinex Ultra Color (from Novozymes), Rohapect Classic (from AB Enzymes), Rohapect 10L (from AB Enzymes). Pectinase may be added in an amount effective in the range from $1.4 \times 10^{9}$-$23500 \times 10^{9}$ Units per ton beer mash.

Proteases as used in the present disclosure are enzymes that catalyze the cleavage of peptide bonds. Suitable proteases include fungal and bacterial proteases. Preferred proteases are acidic proteases, i.e., proteases characterized by the ability to hydrolyze proteins under acidic conditions below pH-7

Suitable acid fungal proteases include fungal proteases derived from *Aspergillus, Mucor, Rhizopus, Candida, Coriolus, Endothia, Enthomophtra, Irpex, Penicillium, Sclerotium* and *Toru-lopsis*. Commercial proteases include GC 106™ and SPEZYME™ FAN (available from Genencor, USA). Suitable bacterial proteases, although not acidic proteases, include the commercially available products ALCALASE™ and NEUTRASE™ (available from Novozymes A/S).

Protease may be added in an amount effective in the range from $0.002'10^{6}$-$314 \times 10^{6}$ Units per ton beer mash.

Any phytase may be used in the methods of the present disclosure. Phytases are enzymes that degrade phytates and/or phytic acid by specifically hydrolyzing the ester link between inositol and phosphorus. Phytase activity is credited with phosphorus and ion availability in many ingredients. In some embodiments, the phytase is capable of liberating at least one inorganic phosphate from an inositol hexaphosphate (e.g., phytic acid). Phytases can be grouped according to their preference for a specific position of the phosphate ester group on the phytate molecule at which hydrolysis is initiated (e.g., 3-phytase (EC 3.1.3.8) or 6-phytase (EC 3.1.3.26)). An example of phytase is myo-inositol-hexakiphosphate-3-phosphohydrolase. Phytases can be obtained from microorganisms such as fungal and bacterial organisms. For example, the phytase may be obtained from filamentous fungi such as *Aspergillus* (e.g., *A. ficuum, A. fumigatus, A. niger*, and *A. terreus*), *Cladospirum, Mucor* (e.g., *Mucor piriformis*), *Mycelioptora* (e.g., *M. termopila*), *Penicillium* (e.g., *P. ordei* (ATCC No. 22053)), *P. piceum* (ATCC No. 10519), or *P. brevi-compactum* (ATCC No. 48944), *Talaromyces* (e.g., *T. thermophilus*), *Thermomyces* (WO 99/49740), and *Trichoderma* spp. (e.g., *T. reesei*). In an embodiment, the phytase is derived from *Buttiauxiella* spp. such as *B. agrestis, B. brennerae, B. ferragutiase, B. gaviniae, B. izardii, B. noackiae,* and *B. warmboldiae*. In some embodiments, the phytase is a phytase disclosed in WO 2006/043178.

Example 1 shows the enzymatic dewatering of the whole stillage after treating the beer mash with enzymes capable of degrading at least one beer mash component. Therefore, one aspect of the disclosure relates to a method to improve the quality of WDG, DDG and/or DDGS comprising the steps of: i) subjecting beer to one or more enzymes capable of degrading one or more beer components, ii) distillation, iii) separating the material into a solid fraction and a liquid fraction. The solid fraction is often referred to as "wet cake" and the liquid fraction is often referred to as "thin stillage".

In accordance with the purposes of the present invention as described herein, in one aspect of the present disclosure a method is provided for improving the nutritional quality of a by-product or residue of a fermentative production process, comprising inoculating the by-product or residue with at least one filamentous fungus, fermenting the by-product or residue and separating at least one enzyme from the fermented by-product or residue; and providing the enzyme to fermented mash (beer mash) of an fermentative production process, preferably an ethanol production process. The filamentous fungus may be selected from the group consisting of *Rhizopus, Aspergillus, Trichoderma*, and any combination thereof. The by-product or residue is preferably a fibrous by-product and may be selected from the group consisting of spent brewer's grains, dried distiller's grains, dried distiller's solubles, distiller's dried grains with solubles and WDG, and mixtures thereof.

In another aspect the present disclosure relates to methods of producing ethanol from starch containing material, said method comprising the steps of:
  v) Converting starch-containing material to fermentable sugars
  vi) Fermentation of the fermentable sugars with a microorganism to fermented mash
  vii) Subjecting the fermented mash after the fermentation process to an enzyme composition comprising an enzyme or a mixture of enzymes
  viii) Separation of the ethanol in the fermented mash by distillation Converting starch-containing material to fermentable sugars can be done by (a) liquefying a starch-containing material and (b) saccharifying the liquefied material obtained in step (a).

The liquefaction is preferably carried out in the presence of an alpha-amylase, preferably a bacterial alpha-amylase or acid fungal alpha-amylase. In an embodiment, a pullulanase, isoamylase, and/or phytase is added during liquefaction.

Preferred organisms for ethanol production are yeasts, such as e.g. *Pichia* or *Saccharomyces*. Preferred yeast according to the disclosure is *Saccharomyces* species, in particular *Saccharomyces cerevisiae* or baker's yeast. The yeast cells may be added in amounts of $10^5$ to $10^{12}$, preferably from $10^7$ to $10^{10}$, especially $5 \times 10^7$ viable yeast count per ml of fermentation broth. During the ethanol producing phase the yeast cell count should preferably be in the range from $10^7$ to $10^{10}$, especially around $2 \times 10^8$. Further guidance in respect of using yeast for fermentation can be found in, e.g., "The alcohol Textbook" (Editors K. Jacques, T. P. Lyons and D. R. Kelsall, Nottingham University Press, United Kingdom 1999), which is hereby incorporated by reference The microorganism used for the fermentation is added to the mash and the fermentation is ongoing until the desired amount of fermentation product is produced; in a preferred embodiment wherein the fermentation product is ethanol to be recovered this may, e.g. be for 24-96 hours, such as 35-60 hours. The temperature and pH during fermentation is at a temperature and pH suitable for the microorganism in question and with regard to the intended use of the fermentation product, such as, e.g., in an embodiment wherein the fermenting organism is yeast and the product is ethanol for recovery the preferred temperature is in the range about 26-34 C, e.g. about 32 C, and at a pH e.g. in the range about pH 3-6, e.g. about pH 4-5.

In another embodiment wherein the fermenting organism is yeast, and the fermented mash is to be used as a beer, the temperature of the mash the preferred temperature is around 12-16 C, such around 14 C.

As mentioned above, the fermenting organism is preferably yeast, e.g., a strain of *Saccharomyces cerevisiae* or *Saccharomyces diastaticus*. In an advantageous embodiment a yeast strain of *Saccharomyces diastaticus* is used (SIHA Amyloferm®, E. Begerow GmbH&Co, Langenlonsheim, Germany) since their exo-amylase activity can split liquid starch and also dextrin, maltose and melibiose.

In the liquefaction step the gelatinized starch (downstream mash) is broken down (hydrolyzed) into maltodextrins (dextrins). To achieve starch hydrolysis a suitable enzyme, preferably an alpha-amylase, is added. Liquefaction may be carried out as a three-step hot slurry process. The slurry is heated to between 60-95° C., preferably 80-85° C., and an alpha-amylase may be added to initiate liquefaction (thinning). Then the slurry may be jet-cooked at a temperature between 95-140° C., preferably 105-125° C., for about 1-15 minutes, preferably for about 3-10 minutes, especially around about 5 minutes. The slurry is cooled to 60-95° C. and more alpha-amylase may be added to complete the hydrolysis (secondary liquefaction). The liquefaction process is usually carried out at a pH of 4.0 to 6.5, in particular at a pH of 4.5 to 6.

The saccharification step and the fermentation step may be performed as separate process steps or as a simultaneous saccharification and fermentation (SSF) step. The saccharification is carried out in the presence of a saccharifying enzyme, e.g. a glucoamylase, a beta-amylase or maltogenic amylase. Optionally a phytase and/or a protease is added.

Saccharification may be carried out using conditions well known in the art with a saccharifying enzyme, e.g., beta-amylase, glucoamylase or maltogenic amylase, and optionally a debranching enzyme, such as an isoamylase or a pullulanase. For instance, a full saccharification process may last up to from about 24 to about 72 hours, however, it is common to do a pre-saccharification for typically 40-90 minutes at a temperature between 30-65° C., typically about 60° C., followed by complete saccharification during fermentation in a simultaneous saccharification and fermentation process (SSF process). Saccharification is typically carried out at a temperature from 20-75° C., preferably from 40-70° C., typically around 60° C., and at a pH between 4 and 5, normally at about pH 4.5.

The most widely used process to produce a fermentation product, especially ethanol, is the simultaneous saccharification and fermentation (SSF) process, in which there is no holding stage for the saccharification, meaning that a fermenting organism, such as a yeast, and enzyme(s), including the hemicellulase(s) and/or specific endoglucanase(s), may be added together. SSF is typically carried out at a temperature from 25° C. to 40° C., such as from 28° C. to 35° C., from 30° C. to 34° C., preferably around about 32° C. In an embodiment, fermentation is ongoing for 6 to 120 hours, in particular 24 to 96 hours.

After the fermentation, the fermented mash is subjected to an enzyme composition according to the present disclosure. In an embodiment, the enzyme composition comprises a beta-1,3-glucanase. In another embodiment the enzyme composition comprises a beta-1,3-glucanase and a 1,6-beta-glucanase. In another embodiment, the enzyme composition comprises a xylanase. In an advantageous embodiment, the enzyme composition comprises a beta-1,3-glucanase and a xylanase. In another embodiment, the enzyme composition comprises a beta-1,3-glucanase, a 1,6-beta-glucanase and a xylanase. In further embodiments, the enzyme composition comprises in addition a pectinase and/or a protease. In an example the enzyme composition comprises a beta-1,3-glucanase, a xylanase and a protease. In another example the enzyme composition comprises a beta-1,3-glucanase, a xylanase and a pectinase. In a further embodiment, enzyme composition comprises a mannanase. In an advantageous embodiment the enzyme composition comprises a mannanase and a beta-1,3-glucanase.

In a particular embodiment, the process of the invention further comprises, prior to liquefying the starch-containing material the steps of:
  reducing the particle size of the starch-containing material, preferably by milling; and
  forming a slurry comprising the starch-containing material and water.

The aqueous slurry may contain from 10-55 w/w % dry solids (DS), preferably 25-45 w/w % dry solids (DS), more preferably 30-40 w/w % dry solids (DS) of the starch-containing material. The slurry is heated to above the gelatinization temperature and an alpha-amylase, preferably a bacterial and/or acid fungal alpha-amylase, may be added to initiate liquefaction (thinning). The slurry may be jet-cooked to further gelatinize the slurry before being subjected to an alpha-amylase in step (a).

In a preferred embodiment, the starch containing material is milled cereals, preferably barley or corn, and the methods comprise a step of milling the cereals before step (a). In other words, the disclosure also encompasses methods, wherein the starch containing material is obtainable by a process comprising milling of cereals, preferably dry milling, e.g. by hammer or roller mils. Grinding is also understood as milling, as is any process suitable for opening the individual grains and exposing the endosperm for further processing. Two processes of milling are normally used in alcohol production: wet and dry milling. The term "dry milling" denotes milling of the whole grain. In dry milling the whole kernel is milled and used in the remaining part of the process Mash formation. The mash may be provided by forming a slurry comprising the milled starch containing material and brewing water. The brewing water may be heated to a suitable temperature prior to being combined with the milled starch containing material in order to achieve a mash temperature of 45 to 70° C., preferably of 53 to 66° C., more preferably of 55 to 60° C. The mash is typically formed in a tank known as the slurry tank.

Subsequent to fermentation the fermentation product may be separated from the fermentation medium. The slurry may be distilled to extract the desired fermentation product or the desired fermentation product from the fermentation medium by micro or membrane filtration techniques. Alternatively the fermentation product may be recovered by stripping. Methods for recovering fermentation products are well known in the art. Typically, the fermentation product, e.g., ethanol, with a purity of up to, e.g., about 96 vol. % ethanol is obtained.

Following the completion of the fermentation process, the material remaining is considered the whole stillage. As used herein, the term "whole stillage" includes the material that remains at the end of the fermentation process both before and after recovery of the fermentation product, e.g., ethanol. The fermentation product can optionally be recovered by any method known in the art. In one embodiment, the whole stillage is separated or partitioned into a solid and liquid phase by one or more methods for separating the thin stillage from the wet cake. Such methods include, for example, centrifugation and decanting. The fermentation product can be optionally recovered before or after the whole stillage is separated into a solid and liquid phase.

Thus, in one embodiment, the methods of the disclosure further comprise distillation to obtain the fermentation product, e.g., ethanol. The fermentation and the distillation may be carried out simultaneously and/or separately/sequentially; optionally followed by one or more process steps for further refinement of the fermentation product.

Figure 2:
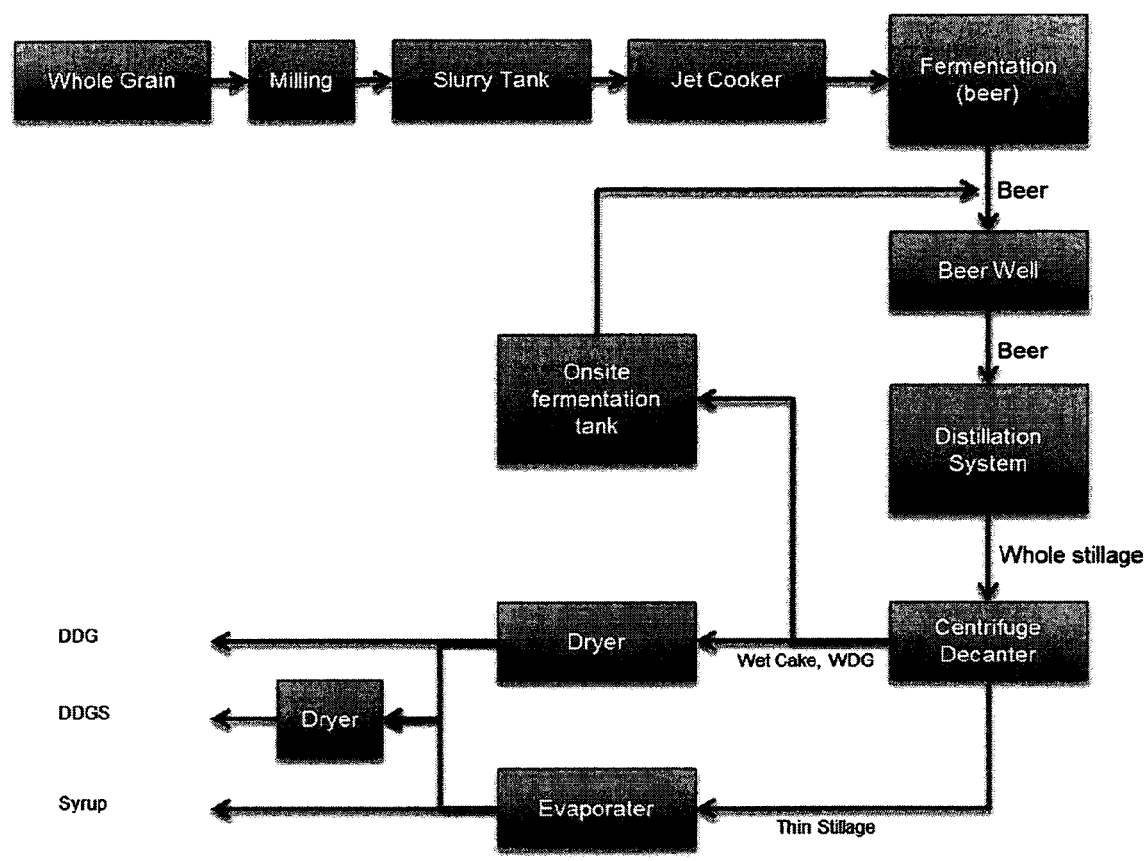
FIG. 2 schematically shows an ethanol process including on site fermentation tank for enzyme production based on WDG.
Figure 3:
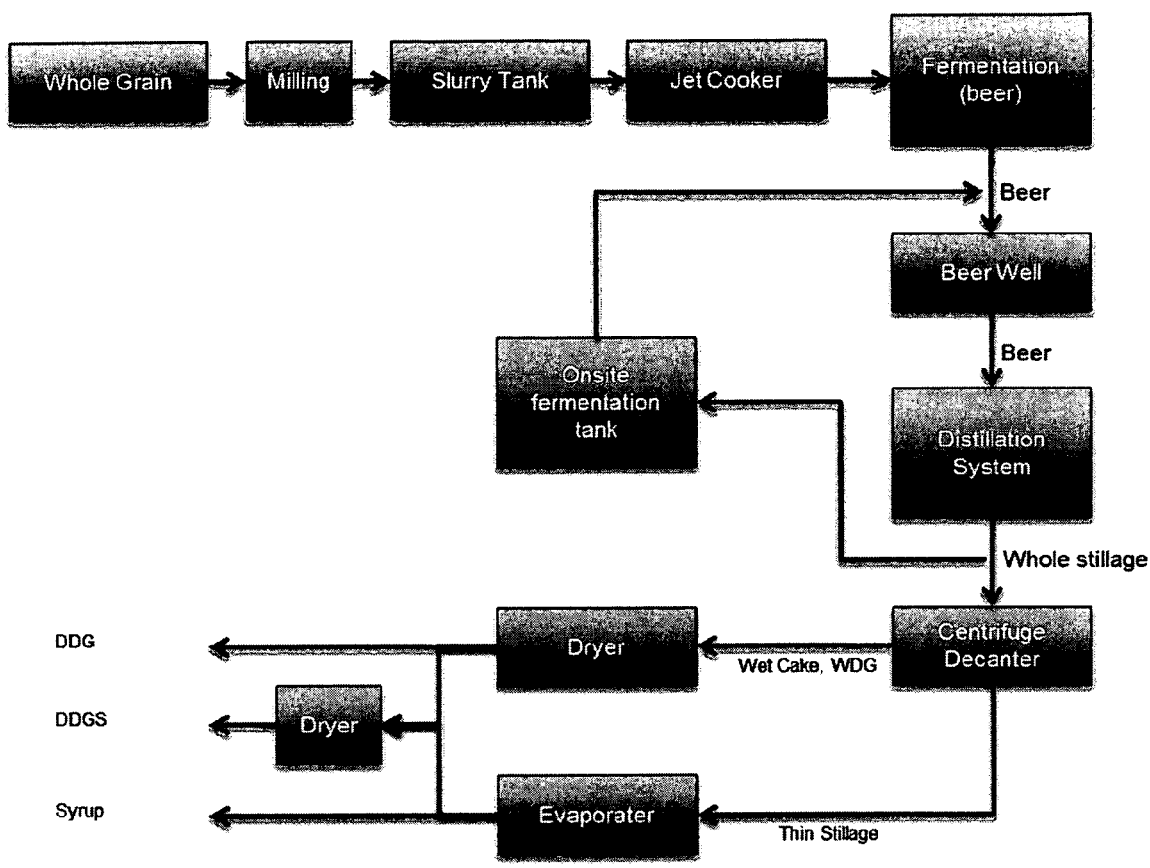
FIG. 3 schematically shows an ethanol process including on site fermentation tank for enzyme production based on whole stillage.

In an embodiment, the aqueous by-product (whole stillage) from the distillation process is separated into two fractions, e.g., by centrifugation: wet grain (solid phase), and thin stillage (supernatant). In another embodiment, the methods of the disclosure further comprise separation of the whole stillage produced by distillation into wet grain and thin stillage; and recycling thin stillage to the starch containing material prior to liquefaction. In one embodiment, the thin stillage is recycled to the milled whole grain slurry. The wet grain fraction may be dried, typically in a drum dryer. The dried product is referred to as distillers dried grains, and can be used as mentioned above as high quality animal feed. The thin stillage fraction may be evaporated providing two fractions (see FIG. 1 and FIG. 2), (i) a condensate fraction of 4-6% DS (mainly of starch, proteins, oil and cell wall components), and (ii) a syrup fraction, mainly consisting of limit dextrins and non-fermentable sugars, which may be introduced into a dryer together with the wet grains (from the whole stillage separation step) to provide a product referred to as distillers dried grain with solubles, which also can be used as animal feed. Thin stillage is the term used for the supernatant of the centrifugation of the whole stillage. Typically, the thin stillage contains 4-6% DS (mainly starch and proteins) and has a temperature of about 60-90° C. In another embodiment, the thin stillage is not recycled, but the condensate stream of evaporated thin stillage is recycled to the slurry containing the milled whole grain to be jet cooked.

Further details on how to carry out liquefaction, saccharification, fermentation, distillation, and recovering of ethanol are well known to the skilled person.

Methods for dewatering stillage and for extracting oil from a fermentation product are known in the art. These methods include decanting or otherwise separating the whole stillage into wet cake and thin stillage. See, e.g., U.S. Pat. Nos. 6,433,146, 7,601,858, and 7,608,729, and U.S. Application Publication No. 2010/0058649. Furthermore, the thin stillage can be evaporated or condensed into syrup or thick stillage from which the oil can be extracted utilizing centrifugation, filtering, heat, high temperature, increased pressure, or a combination of the same. Another way to extract oil is to lower the pH of the thin stillage or syrup. The use of surfactants to break emulsions also enhances oil extraction. Presses can also be used for dewatering. In one embodiment of the disclosure, the presence of beta 1,3-glucanase and/or xylanase in the fermented mash after the fermentation increases the amount of oil in the thin stillage and further the syrup or thick stillage.

The fermentation product(s) can be optionally recovered from the fermentation medium using any method known in the art including, but not limited to, chromatography, electrophoretic procedures, differential solubility, distillation, or extraction. For example, alcohol is separated from the fermented cellulosic material and purified by conventional methods of distillation as mentioned above. Ethanol with a purity of up to about 96 vol. % can be obtained, which can be used as, for example, fuel ethanol, drinking ethanol, i.e., potable neutral spirits, or industrial ethanol.

The inventions described and claimed herein are not to be limited in scope by the specific embodiments herein disclosed, since these embodiments are intended as illustrations of several aspects of the invention. Any equivalent embodiments are intended to be within the scope of this invention. Indeed, various modifications of the invention in addition to those shown and described herein will become apparent to those skilled in the art from the foregoing description. Such modifications are also intended to fall within the scope of the appended claims. In the case of conflict, the present disclosure including definitions will control. Various references are cited herein, the disclosures of which are incorporated by reference in their entireties. The present invention is further described by the following examples which should not be construed as limiting the scope of the invention.

EXAMPLES

A) Processes for Producing Fermentation Products
In one embodiment, the process of the production of ethanol form corn was performed as follows:
a) reducing the particle size of the starch-containing material by milling:
corn was milled to <2 mm particle size b) forming a slurry comprising the starch-containing material and water
10 kg corn were mixed with tap water at 35° C. to obtain a ~31.25% solid solution, total volume 30 liter
pH range was 5.6-6.0
c) liquefying of the starch-containing material
temperature was increased to 90° C.
7 ml alpha-amylase (Novozymes Liquozyme SC) were added
1‰ antifoam was added (30 ml)
incubation for 90 min at 90° C. and stirring at 150 rpm
d) saccharifying of the liquefied material obtained
slurry was cooled to 30° C., pH adjusted to ~4 with 1M (NH4)2SO4-12 ml Glucoamylase (Novozymes Spirizyme Ultra) was added
e) fermentation
Yeast propagation: 200 ml YNB-starch medium was incubated overnight (30° C., 150 rpm) and inoculated with 2 g yeast (SIHA Amyloferm), the complete pre-culture was added to the fermentation
addition of 10 g ($(NH_4)_2SO_4$) as nitrogen source
yeast addition
pH was titrated to 4.0 with ammoniac solution (25%),— incubation for max. 48 h at 30° C. and 100 rpm
2-ml samples were taken every 12 hrs to monitor fermentation progress (sugar-, ethanol concentration)
B) Enzymes:
The following enzymes listed in Table 1 were used alone or in different combinations.

TABLE 1

| Typ | Activity | Shortname |
|---|---|---|
| Cellulase | 565.84 U/g | Cel2 |
| endo-1,4 beta Mannanase | 6538.01 U/g | Man3 |
| Pectinase | 90349.55 U/ml | Pec3 |
| β 1-3 Glucanase | 10016.97 U/g | Glu1 |
| Xylanase | 34094.02 U/g | Xyl4 |
| Xylanase | 35094.00 U/g | Xyl7 |

C) Enzyme Product Activity Determination with DNSA:
Substrates: -endo Glucanase: β-Glucan from barley, low viscosity (Megazyme)
Xylanase: Xylan from Birchwood (Sigma)
Mannanase: Galactomannan, carob
Pectinase: Polygalacturonic acid (Sigma)
Substrates were dissolved in buffer to a concentration of 0.8% (w/v)
Buffer: 50 mM NaAcetat, pH 4.5
The Enzymes were diluted in buffer, the right enzyme concentration must be determined for each enzyme. A 90 μl substrate and 10 μl enzyme solution were mixed. A blank was measured replacing enzyme solution with water. Incubation for 30 min at 37° C. (Reducing sugars were measured after mixing of 50 μl of the incubated substrate—enzyme mix with 50 μl DNSA-Reagent.
The activity is calculated as Units per μl or mg of enzyme product. 1 unit is defined as the amount of formed reducing ends in μmol per minute.
D) ASSAY on endo-1,3-Beta-Glucanase
The substrate employed is Azurine-crosslinked pachyman (AZCL-Pachyman).The substrate is prepared by dyeing and crosslinking highly purified pachyman to produce a material which hydrates in water but is water insoluble. Hydrolysis by endo-1,3-β-glucanase produces water soluble dyed fragments, and the rate of release of these (increase in absorbance at 590 nm) can be related directly to enzyme activity. The substrate is supplied commercially in a ready-to-use tablet form as 1,3-Beta-Glucazyme Tablets (Megazyme International Ireland Ltd, 1,3-BETA-GLUCAZYME TABLETS)

E) Protease Assay

Protease activity of enzyme products was determined with TNBS-Assay as described in Example 6.

One protease unit is defined as the formation of glycin equivalents per minute. The enzyme activities are shown in Table 2.

TABLE 2

| Shortname | Main Activity | Unit |
|---|---|---|
| Cel1 | 79.64 | U/ml |
| Cel2 | 565.84 | U/g |
| Cel3 | 1061.00 | U/ml |
| Man1 | 6205.96 | U/g |
| Man2 | 7988.38 | U/g |
| Man3 | 6538.01 | U/g |
| Pec1 | 28242.70 | U/ml |
| Pec2 | 37473.18 | U/ml |
| Pec3 | 90349.55 | U/ml |
| Pec4 | 117283.35 | U/ml |
| Pec5 | 44082.56 | U/ml |
| Glu1 | 10016.97 | U/g |
| Glu2 | 10594.57 | U/g |
| Glu3 | 3583.18 | U/g |
| Glu5 | 763.00 | U/ml |
| Xyl1 | 2264.56 | U/ml |
| Xyl2 | 4434.68 | U/g |
| Xyl3 | 314.83 | U/g |
| Xyl4 | 34094.02 | U/g |
| Xyl5 | 4.28 | U/g |
| Xyl7 | 35094.00 | U/g |
| Xyl8 | 14108.00 | U/g |
| Xyl9 | 75000.00 | U/g |
| Xyl10 | 790.00 | U/g |
| Xyl11 | 1178.00 | U/g |
| Xyl12 | 16603.50 | U/g |

Example 1

Dewatering of Whole Stillage

Beer (8.7 wt-% dry solids, pH-4.0 from conventional, dry-milled ethanol fermentation was used as substrate.

An aliquot (50 mL) of whole stillage was placed into a centrifuge tube and heated to 37<0>C. Total enzyme concentration added was 200 ppm, the mixture was gently agitated overnight on a rotary shaker.

The tube was centrifuged for 5 minutes at 2000 rpm. The supernatant was decanted and the resulting wet cake was weighed and compared to the control without addition of any enzyme. The results, along with several enzymes and enzyme combinations tested, are shown in Table 2 and Table 3.

TABLE 2

| Enzyme | wet cake | StdDev |
|---|---|---|
| Cel1 | 91.9% | 1.15 |
| Cel2 | 90.8% | 1.06 |
| Man1 | 87.8% | 4.01 |
| Man2 | 86.7% | 2.53 |
| Man3 | | |
| Men1 | 99.6% | 0.4 |
| Pec1 | 97.8% | 2.48 |
| Pec2 | 87.1% | 8.16 |
| Pec3 | 80.8% | 0.71 |
| Pec4 | 82.0% | 0.57 |
| Pec5 | 94.6% | 3.65 |

TABLE 2-continued

| Enzyme | wet cake | StdDev |
|---|---|---|
| Pro1 | 87.8% | 1.12 |
| Pro2 | 96.2% | 0.89 |
| Pro3 | 93.7% | 1.34 |
| Pro4 | 91.5% | 1.97 |
| Pro5 | 93.3% | 4.77 |
| Glu1 | 85.8% | 1.33 |
| Glu2 | 79.6% | 0.81 |
| Glu3 | 90.3% | 0.65 |
| Xyl1 | 79.4% | 1.29 |
| Xyl2 | 91.3% | 1.17 |
| Xyl3 | 86.1% | 1.16 |
| Xyl4 | 77.0% | 0.92 |
| Xyl5 | 90.1% | 0.41 |
| Xyl6 | 89.6% | 2.05 |

TABLE 3

| Enzyme combinations | Wet cake | StdDev |
|---|---|---|
| Xyl4 | 87.4% | 0.23 |
| Xyl4 + Glu1 | 83.1% | 0.26 |
| Xyl4 + Pec3 | 86.7% | 0.63 |
| Xyl4 + Man3 | 82.7% | 0.30 |
| Xyl4 + Cel2 | 88.3% | 0.05 |
| Xyl4 + Pro1 | 87.4% | 0.58 |
| Xyl4 + Glu1 + Prot1 | 78.5% | 0.07 |
| Xyl4 + Pec3 + Prot1 | 82.6% | 0.20 |
| Xyl4 + Man3 + Prot1 | 82.5% | 0.13 |
| Xyl4 + Cel2 + Prot1 | 82.7% | 0.19 |
| Xyl4 + Pec3 + Man3 | 82.7% | 0.19 |
| Xyl4 + Cel2 + Man3 | 83.2% | 0.11 |
| Xyl4 + Cel2 + Pec3 | 82.6% | 0.13 |
| Xyl4 + Pec3 + Glu1 | 81.4% | 0.04 |

Example 2

Fiber Reduction in DDGS After Enzymatic Treatment Measured by Determination of ADF and NDF Acid Detergent Fibers (ADF) and Neutral Detergent Fibers (NDF) are dietary fibers and can be soluble and insoluble. ADF containing lignin and cellulose, NDF is containing ADF and hemicelluloses. Soluble fibers are responsible for viscosity effects within the digestion process and responsible for reduce energy and protein uptake (cage effect). Reduced ADF/NDF values leads to better digestion within the intestinal due to the reduced viscosity in coincidence with better protein and energy release.

Beer (10 wt-% dry solids, pH=4.0) from conventional, dry-milled ethanol fermentation was used as substrate.

An aliquot (50 mL) of beer was placed into a centrifuge tube and heated to 37° C. The total enzyme amount added was in the range of 100 ppm to 400 ppm, the mixture was gently agitated for 6 hours on a rotary shaker. After thermal enzyme inactivation (1 hour at 80° C.) the whole stillage was dried and milled. The dried stillage was analyzed for ADF/NDF according the protocols of VDLUFA Bd. III, 6.5.2. (Method book III "The chemical analysis of feedstuff" of VDLUFA 1st-7th supplement delivery)

Figure 4:
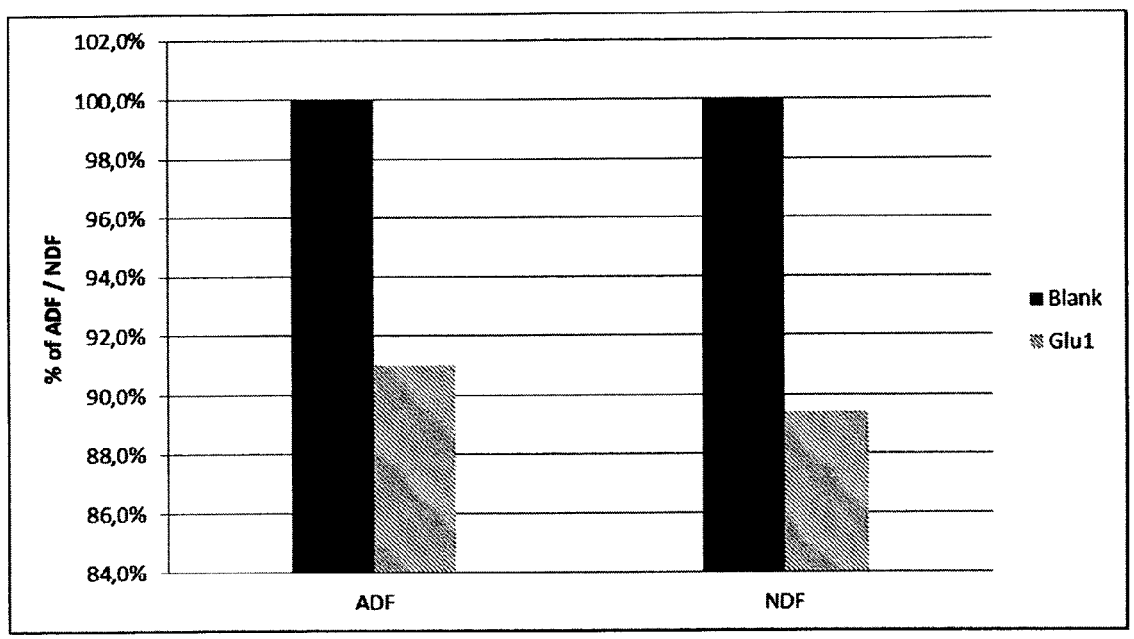
FIG. 4 is a diagram showing the reduction of ADF and NDF in DDGS by using 1,3-β-glucanase.

The results are shown FIGS. 4 to 7. FIG. 4 shows the result of adding an enzyme composition comprising beta-1,3-glucanase as the main activity (Rohalase BX, AB Enzymes). The measured parameters are Neutral Detergent Fibers (NDF) and Acid Detergent Fibers (ADF). The enzyme dosage was 200 g/t of beer. These results shows clearly that the beta-1,3-glucanase enzyme reduces the values of ADF and NDF by 9% and 10.6%.

Figure 5:
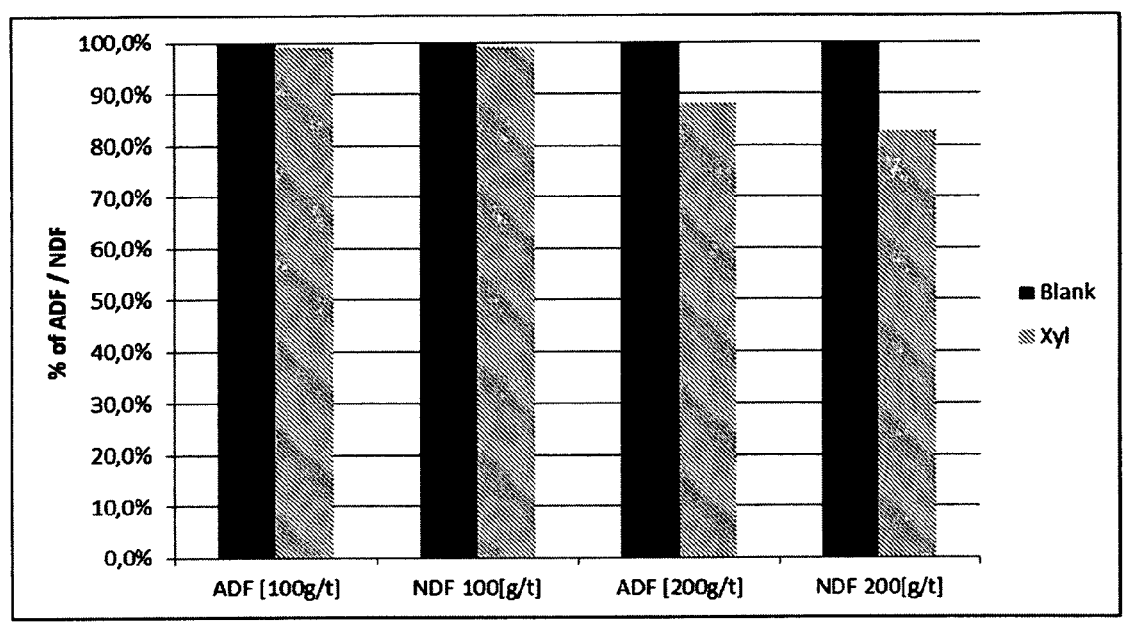
FIG. 5 is a diagram showing the reduction of ADF and NDF in DDGS by using xylanase.

FIG. 5 shows the effect of an enzyme composition comprising a xylanase as the main activity (Xylanase 2 XP Conc, Dyadic) applied in two concentrations of 100 and 200 g/t of beer. The xylanase reduces the fiber content of DDGS which can be seen in the clear reduction of ADF and NDF. With an enzymes dosage of 100 g/t the NDF concentration is only reduced by 1.2% whereas the reduction was 17.3% for a dosage of 200 g/t.

Figure 6:
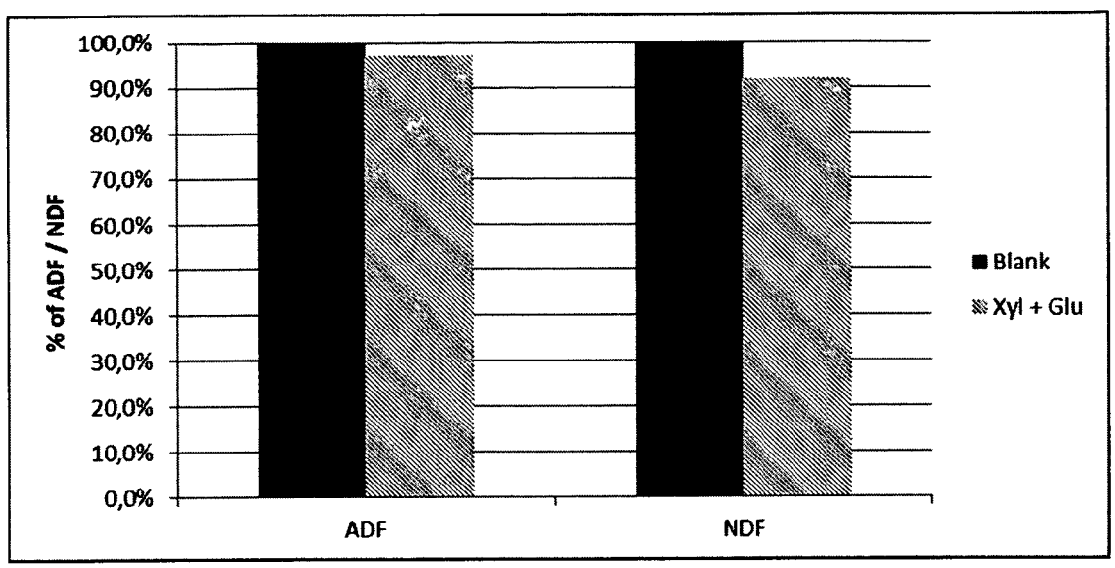
FIG. 6 is a diagram showing the reduction of ADF and NDF in DDGS by using an enzyme composition comprising 1,3-β-glucanase and xylanase.

FIG. 6 shows the effect of an enzyme composition comprising as main activities xylanase and 1,3-beta-glucanase activity, added in concentrations of each 200 g/t beer.

Compared to FIG. 5 where xylanase used in a concentration of 100 g/t alone showed only minimal effect on fiber reduction, the combination of xylanase and 1,3-beta-glucanase has a higher effect. The ADF value is reduced by 2.8% and the NDF value by 8.2%.

Figure 7:
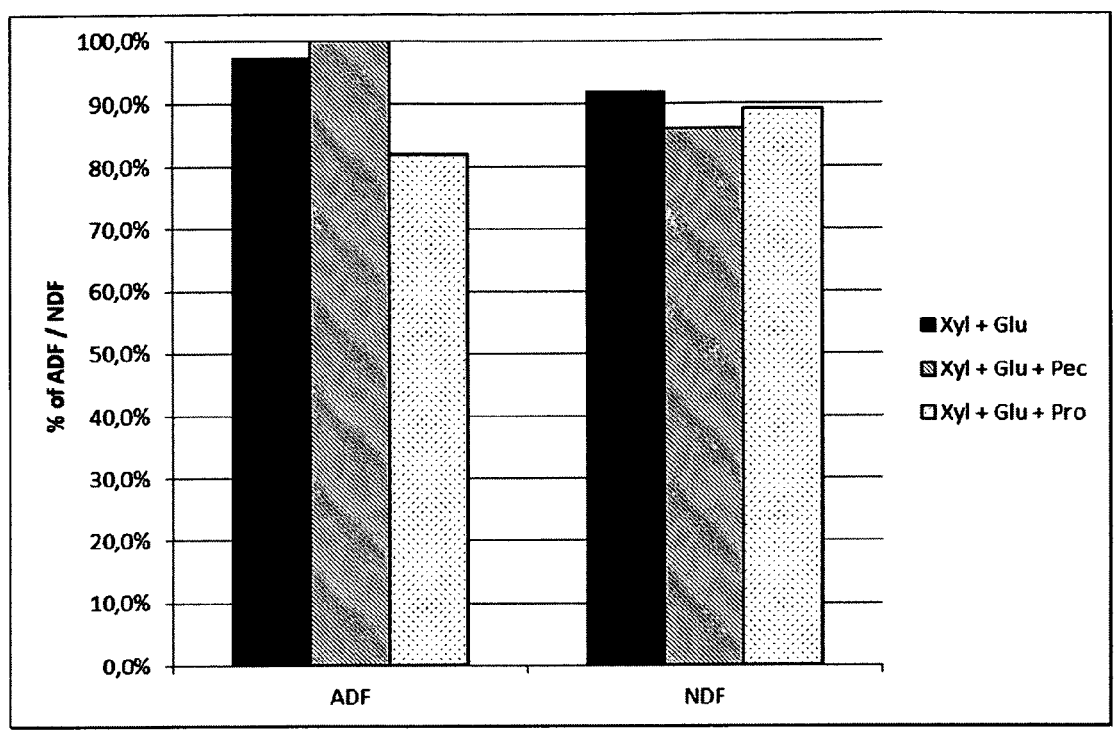
FIG. 7 is a diagram showing the reduction of ADF and NDF in DDGS by using an enzyme composition comprising 1,3-β-glucanase and xylanase and a pectinase or a protease.

FIG. 7 shows the ADF/NDF reduction of the combination of xylanase and 1,3-beta-glucanase in two combinations each with additional enzymes. An enzyme composition comprising in addition pectinase activity (Rohapect Classic, AB Enzymes) is showing an additional reduction of NDF (5.8%) but the enzyme is overriding the effect for ADF. The additional application of proteases (Protease A, Amano Japan) is affecting the ADF and NDF reduction positive. The NDF value is reduced again by 3.2%.

Example 3

De-Oiling Improvement

The oil content of DDGS is sometimes higher than desired and methods of recovering more oil as a separate by-product for use in biodiesel production or other biorenewable products are sought. Much of the work in oil recovery from fermentation processes has focused on improving the extractability of the oil from the whole stillage. As mentioned in the specification, a better de-oiling leads to a better oil separation within the ETOH process. The corn oil production is a high valuable byproduct for the food and feed industry also for the Biodiesel production.

Figure 8:
FIG. 8 showing a picture of thin stillage from not enzyme treated beer, whereby no oil separation can be shown.
Figure 9:
FIG. 9 showing a picture of thin stillage from enzyme treated beer, whereby a clear separation of the oil forming in thick oil layer is shown.

After the reaction of an enzyme composition comprising as main activities xylanase (200 ppm, Xylanase 2 XP Conc, Dyadic) and 1,3-beta-glucanase activity (200 ppm, Rohalase BX, AB Enzymes), followed by the centrifugation (conditions: 3000 rpm for 10 min.) of the whole stillage an improved oil separation in the thin stillage was observed. FIGS. 8 and 9 are showing results of thin stillages after centrifugation. The thin stillage where the beer was treated with the enzyme composition comprising as main activities xylanase and 1,3-glucanase activity (FIG. 9) shows a much bigger oil layer on the supernatant compared to the thin stillage where the beer was not treated with enzymes (FIG. 8). FIG. 8 shows that no oil separation has been adjusted. FIG. 9 shows that a clear separation of oil, forming a thick oil layer can be observed.

Example 4

Feeding Tests

With the following animal trial it was shown that the exchange of expensive feed ingredients, like soybean meal, corn or wheat, with DDGS, especially DDGS that is modified during the production processes and methods according to the present disclosure, is possible and do not results in lower weight gains. The goal was to show that DDGS-treated can replace Soybean meal and wheat without negative effects on animal growth.
- quails as tests animals fed from day 1-day 23
- Replicates 10 cages with 2 animals for each treatment
- DDGS inclusion in feed 20%
- positive control was standard wheat and soybean meal diet without DDGS
- All feed ratios were balanced to be isonitrogen (every feed contains the same amount of CP) and isocaloric (each feed contains the same amount of metabolized energy)
- 3 animal groups with normal feed, untreated DDGS and enzymatically optimized DDGS
- Performance parameters: weight gain, Feed conversion ration For the tests, two Different DDGS types were produced:
a) DDGS resulting from a treatment of the fermented mash in the ethanol production from A) of the present disclosure with an enzyme composition comprising a xylanase (200 ppm, Xylanase 2 XP Conc, Dyadic) and a 1,3-glucanase (200 ppm, Rohalase BX, AB Enzymes) (DDGS-treated)
b) DDGS produced without an enzyme treatment of the fermented mash (DDGS-blank).

Figure 10:
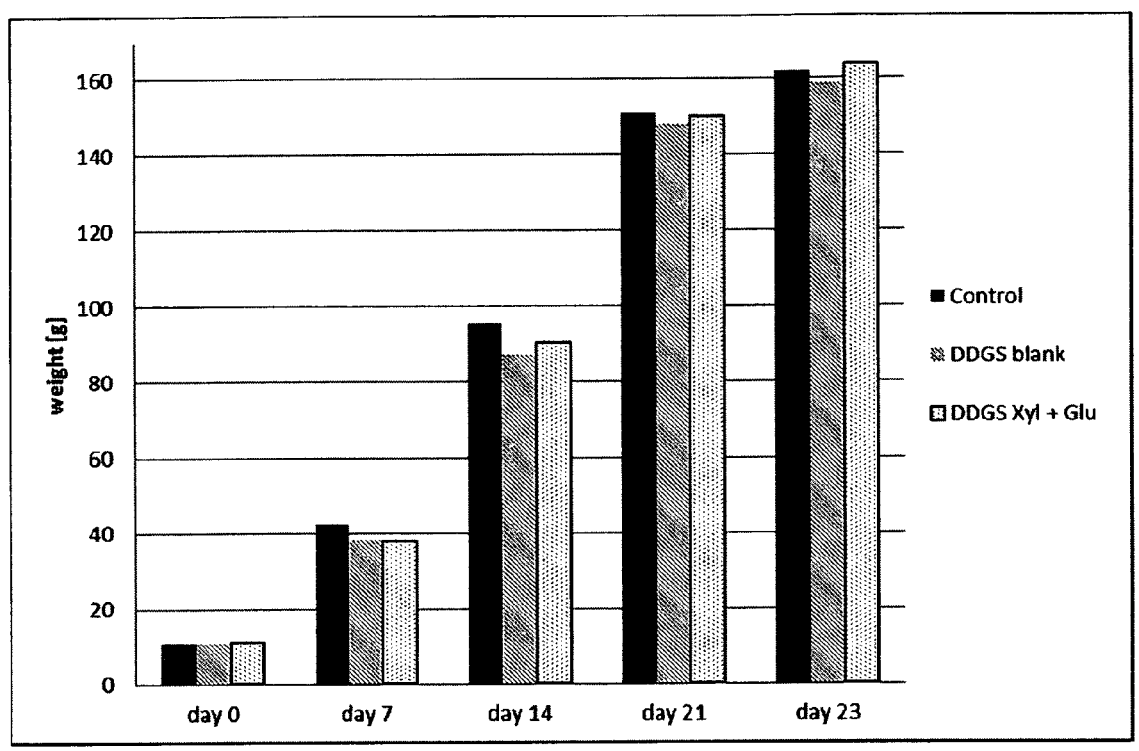
FIG. 10 is a diagram showing the weight gain of quails fed with different feed stuff.

As a positive control a standard quail feed was used. FIG. 10 shows the results and the weight gain of quails fed with different feed stuff. In the starter phase (day 0-14) the normal feed leads to highest weight gain. In the grower phase, feed with 20% of the DDGS-treated, lead to the highest weight gain and outperformed the other two feeds. Based on the animal trial data, the feed containing DDGS-treated is showing a clear outperformance. The DDGS-treated can be included to quail feed at a concentration of 20% without negative effects on growth performance.

Example 5

De-Watering of Whole Stillage

As mentioned above in the specification, a better de watering capability of the whole stillage results in a wet cake with a higher dry mass. The advantage here is less energy consumption while drying.

For that example the de watering capability of the whole stillage during the centrifugation was tested and determined. Two different setups were tested. In the first test the beer after the fermentation was not treated with enzymes (DDGS blank), within the second test the beer was treated with the enzyme composition comprising a xylanase (200 ppm,) and a 1,3-glucanase (200 ppm) after the fermentation (DDGS treated).

The trials were performed on a 30 l scale. Each test was carried out as duplicate. The total enzyme concentration added was 400 g/t of beer. After the distillation the fermenter was drained off and the whole stillage was centrifuged to obtain thin stillage and the wet cake.

30 l Corn to Ethanol fermentation with enzyme application and DDGS production:
- pre milled corn <2 mm particle size
- 10 kg corn were mixed with tap water at 35° C. t to reach a concentration of ~32% (w/w)
- pH range was 5.6-6.0
- temperature was increased to 90° C.
- 7 ml alpha-amylase (Liquizyme from Novozymes) were added
- 1‰ antifoam was added (30 ml)
- incubation for 90 min at 90° C. and 150 rpm
- 12 ml Glucoamylase (Novozymes Spirizyme Ultra) was added
- addition of 300 ppm ((NH4)2SO4) as nitrogen source
- direct inoculation with dry yeast
- pH adjustment to pH 5.5
- fermentation for 62 h at 33° C. and 150 rpm to obtain the beer
- The beer is than treated with enzymes for 6 hours at 37° C.
- after 68 hours ethanol is removed by distillation obtaining a residue called whole stillage
- afterwards the whole stillage is centrifuged at 3000 rpm resulting in thick stillage and thin stillage concentration of the thin stillage to 50% DM by evaporation—The wet cake is mixed with the thin stillage and dried in a drum dryer at ca. 120° C. up to a 90% dry matter.

Figure 11:
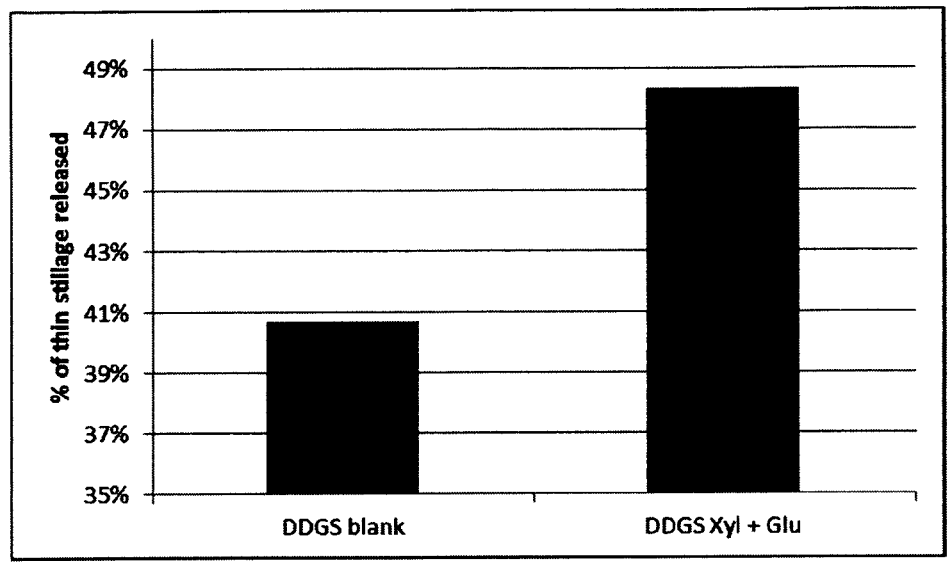
FIG. 11 is a diagram showing the dewatering capabilities of an enzyme based process according to the present disclosure by using an enzyme composition comprising 1,3-β-glucanase and xylanase.

FIG. 11 shows the amount of thin stillage (supernatant) in % of whole stillage removed after centrifugation at 3000 rpm for 10 minutes. Here it was shown that a treatment with the enzyme composition comprising a xylanase and a 1,3-glucanase increases the dewatering capability by 18.7%.

Example 6

In-vitro Digestibility of DDGS

In vitro digestibility assays, (simulating the digestion in animals) are well accepted to predict the digestibility of feed stuff.

Two different setups were tested. In the first test the beer after the fermentation was not treated with enzymes (DDGS-blank), for the second test the beer was treated with the enzyme composition comprising a xylanase (200 ppm) and a 1,3-glucanase (200 pm) after the fermentation (DDGS treated).

In the following the In vitro protein digestibility assay is described:

DDGS samples are digested by a Pepsin/HCl solution: 0.1 M HCl with 20mg/ml Pepsin. (Pepsin from porcine gastric mucosa, powder, 400-800 units/mg protein, Sigma: P7125) The supernatant is used for the determination of free amino groups by the TNBS assay.

Protein Digestion:
  0.5 g DDGS is mixed with 8 ml of 0.1M HCl with 20 mg/ml Pepsin.
  After mixing with a Vortexer the samples are incubated for 60 min at 40° C.
  After 60 min. the sample is centrifuged for 20 min at 4000 rpm.
  After the centrifugation the protein is measured in the supernatant Protein Determination with TNBS-Assay:
  2,4,6-Trinitrobenzene Sulfonic Acid (TNBSA or TNBS (2,4,6-Trinitrobenzene Sulfonic Acid) is a rapid and sensitive assay reagent for the determination of free amino groups. Primary amines, upon reaction with TNBSA, form a highly chromogenic derivative, which can be measured at 335 nm (see figure). Qualitative measurements of amines, sulfhydryls or hydrazides, 3 and quantitative measurements of free-amino groups of L-lysine have also been obtained using TNBSA.

Preparation of Buffers

| No | Component |
|----|-----------|
| 1  | 1% SDS |
| 2  | 0.1M HCl |
| 3  | 0.025% TNBS in 87.5 mM Na-Phosphat pH 8.2 |
| 4  | 100 mM Glycin stock in 1% SDS |

Sampling (in 96-Well-Plate):
1. For standard curve:
   Glycin start 2500 µM, 2× diluted in 1% SDS

| Glycin row |
|------------|
| 2500 |
| 1250 |
| 625 |
| 312.5 |
| 156.25 |
| 78.125 |
| 39.0625 |
| 0 |

2. Samples, (diluted 1000×) with 1% SDS

Reaction (96 Well PCR Plate):
  1. 15 µl of Glycin row or samples+90 µl of buffer No 3 (see buffer list)
  2. PCR plate is incubated in PCR cycler, program:
     50° C. for 30 min
     4° C. for 10 min
  3. Take out from PCR cycler, mix properly Measurement:
  50 µl of step 3 above are mixed with 50 µl of buffer No 2 (see buffer list), absorption is measured at 340 nm Two different setups were tested. In the first test the beer after the fermentation was not treated with enzymes (DDGS-blank), for the second test the beer was treated with an enzyme composition comprising a xylanase and a 1,3-glucanase as main activities after the fermentation (DDGS-treated).

Figure 12:
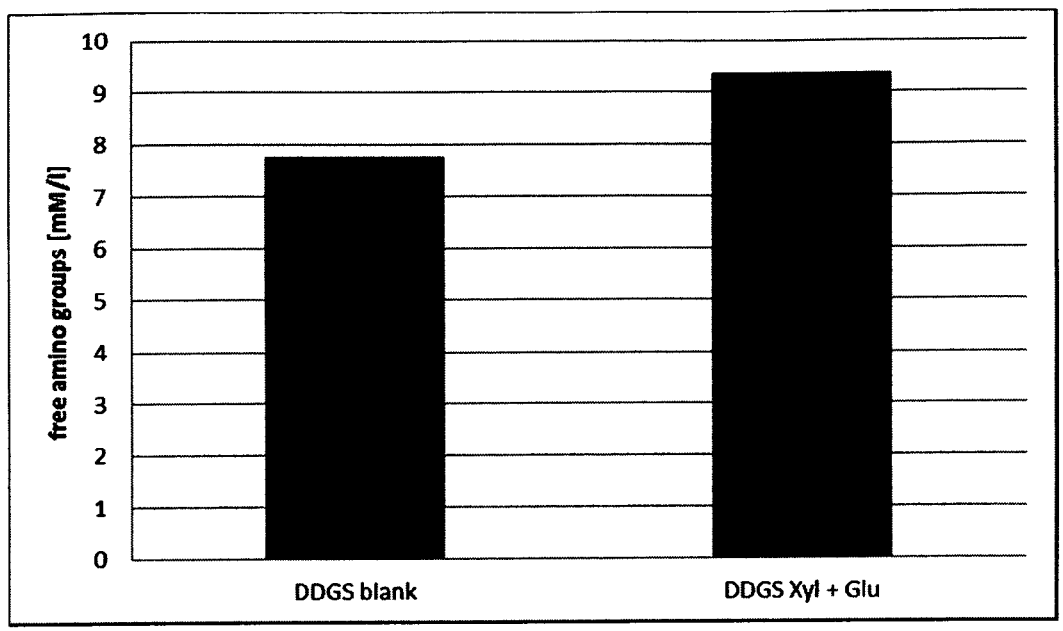
FIG. 12 is a diagram showing an in vitro-digestibility assay of DDGS produced using an enzyme composition comprising 1,3-β-glucanase and xylanase in a process according to the present disclosure.

The enzyme treated DDGS was produced with the enzyme composition comprising a xylanase and a 1,3-glucanase as main activities with a total concentration of 400 g/t beer. FIG. 12 is showing the results.

FIG. 12 shows the release of free amino groups with different substrates. The DDGS-treated shows an increased concentration of free amino groups by 20.4%, determined by TNBS assay Therefore it can be clearly shown that compared to the DDGS-blank the protein digestibility with Pepsin/HCL is increased by DDGS-treated. This results in an improved nutritional quality of the DDGS as a by-product of the fermentation process and therefore is a high quality animal feed.

Example 7

Protein Solubilisation in Water

Two different setups were tested. In the first test the beer after the fermentation was not treated with enzymes (DDGS-blank), for the second test the beer was treated with the enzyme composition comprising a xylanase (200 ppm) and a 1,3-glucanase (200 pm) after the fermentation (DDGS treated).

For that test 0.5 g DDGS was mixed with 8 ml distilled water and shacked with a Vortexer. The solution was incubated for 60 min at 40° C. After a centrifugation step (20 min, 4000 rpm, 4° C.) the protein concentration in the supernatant was analyzed with the TNBS assay (see example 6).

Figure 13:
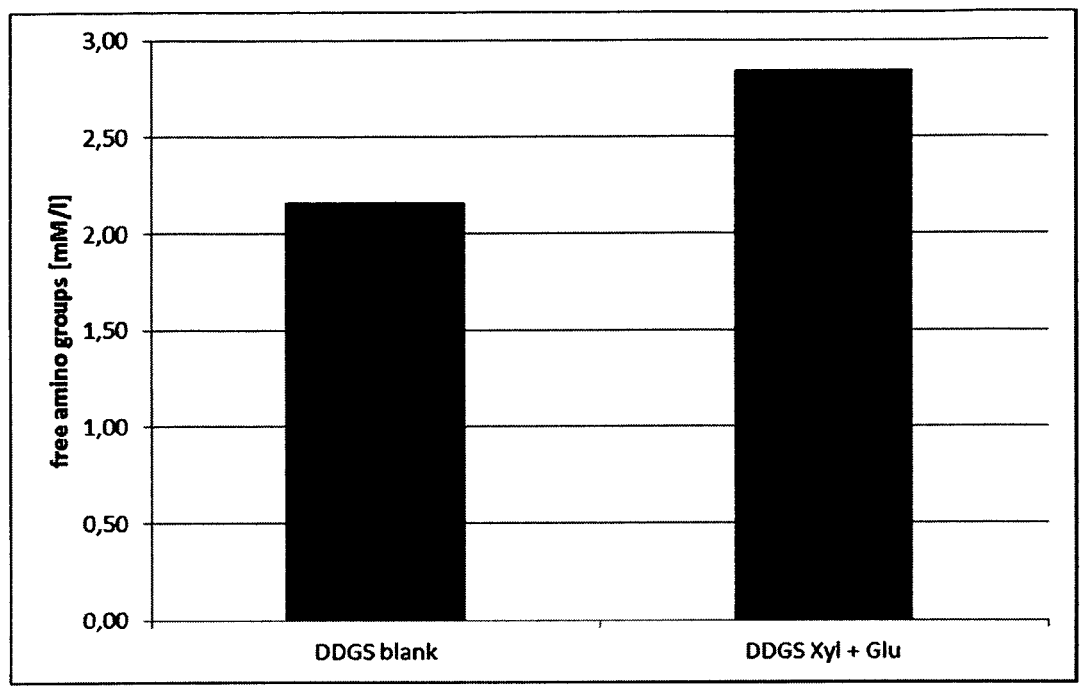
FIG. 13 is a diagram showing the improved protein availability of DDGS produced using an enzyme composition comprising 1,3-β-glucanase and xylanase in a process according to the present disclosure.

In FIG. 13 the release of free amino groups of DDGS in water is shown. The DDGS-treated is showing an increase of free amino groups by 31.4%. The fiber structure of the DDGS is changed as well as the yeast cell walls are disrupted resulting in an increased availability of proteins that can be readily digested in the animal.

This result in an improved nutritional quality of the DDGS as a by-product of a fermentation process and therefore in a high quality animal feed.

Some embodiments of the present disclosure pertain to:
  A) Methods to improve the quality of by-products or residues derived from fermented mash comprising the steps of: i) subjecting the fermented mash during or after the fermentation to a composition comprising an enzyme or a mixture of enzymes capable of degrading one or more fermented mash components, ii) separating the desired fermentation product, wherein the fermented mash can be derived from a process of producing a liquid fermentation product.

the fermented mash can be derived from a process of producing a fermentation product utilizing sugar-containing material as feedstock.

the fermented mash can be derived from a process of producing a fermentation product utilizing starch-containing material as feedstock.

the feedstock can be a cereal.

the feedstock can be selected from the group consisting of corn, wheat, barley, triticale, cassava, sorghum, rye, potato, or any combination thereof.

the liquid fermentation product can be an alcohol, preferably ethanol.

the composition may comprise an enzyme selected from the group consisting of amylase, such as alpha-amylase, glucoamylase, cellulase, beta-glucanase, hemicellulase, such as xylanase, pectinase, mannanase, and protease, or a mixture thereof.

the composition may comprise a mannanase.

the composition may comprises a mannanase and a beta-glucanase.

the desired fermentation product may be separated by distillation.

B) Methods for improving the nutritional quality of a by-product or residue of a fermentative ethanol producing process, comprising the following steps:

i) Fermentation of fermentable sugars with a microorganism ii) Subjecting the fermented mash to a composition comprising an enzyme or a mixture of enzymes after the fermentation process iii) Separation of the ethanol iv) Separation of the by-product or residue, wherein the by-product or residue may be selected from the group consisting of spent brewer's grains, dried distiller's grains, dried distiller's solubles, distiller's dried grains with solubles, residues of the cereal processing industry, wheat bran, soybean hulls, citrus pulp, beet pulp, rice husks or hulls, bagasse, apple pommace, and mixtures thereof.

step iii) and iv) can be carried out simultaneously or sequentially.

the composition may comprise an enzyme selected from the group consisting of amylase, such as alpha-amylase, glucoamylase, cellulase, beta-glucanase, hemicellulase, such as xylanase, pectinase, mannanase, and protease, or a mixture thereof.

the composition may comprise a mannanase.

the composition may comprise a mannanase and a beta-glucanase.

C) Methods of dewatering whole stillage comprising the steps of i) subjecting beer mash to one or more enzymes capable of degrading one or more beer mash components, ii) separating ethanol from the beer mash, iii) separating whole stillage into a solid fraction and a liquid fraction.

D) Methods of producing ethanol, said method comprising the steps of:

i) Fermentation of fermentable sugars with a microorganism to produce ethanol ii) Subjecting the fermented mash to a composition comprising an enzyme or a mixture of enzymes after the fermentation process iii) Separation of the ethanol, wherein the fermented mash can be subjected to the enzyme composition after the fermentation step and before the separation step.

the separation step can be distillation.

the composition may comprise an enzyme selected from the group consisting of amylase, such as alpha-amylase, glucoamylase, cellulase, beta-glucanase, hemicellulase, such as xylanase, pectinase, mannanase, and protease, or a mixture thereof.

the composition may comprise a mannanase.

the composition may comprise a mannanase and a beta-glucanase.

E) Methods to improve the quality and nutritional composition of by-products or residues derived from fermentable sugars in an ethanol producing process comprising the steps of: i) subjecting the fermented mash to a composition comprising an enzyme or a mixture of enzymes capable of degrading one or more fermented mash components, ii) separating the ethanol and the by-products or residues, wherein the fermented mash can be subjected to the enzyme composition after the fermentation step and before the separation step.

the separation step may be distillation.

the composition may comprise an enzyme selected from the group consisting of amylase, such as alpha-amylase, glucoamylase, cellulase, beta-glucanase, hemicellulase, such as xylanase, pectinase, mannanase, and protease, or a mixture thereof.

the composition may comprise a mannanase.

the composition may comprises a mannanase and a beta-glucanase.

the fermentation can be performed using a microorganism, such as bacteria, yeast or fungi.

F) Methods of dewatering whole stillage comprising one of the above mentioned methods and the steps of i) subjecting whole stillage to one or more enzymes capable of degrading one or more whole stillage components, ii) separating the material into a solid fraction and a liquid fraction.

G) Use of a hemicellulase for the degradation of fermented mash components in a fermentative production process.

H) Use of xylanase, amylase, glucoamylase, cellulase, hemicellulase, pectinase, or protease, or a mixture thereof, for the degradation of fermented mash the components in a fermentative production process.

I) Methods for the manufacturing of an enzymes composition used for treating fermented mash of in an fermentative production process to improve the nutritional quality of a by-product or residue and/or the process ability of the production process, comprising:

a) inoculating the by-product or residue with at least one filamentous fungus;

b) fermenting the by-product or residue; and c) separating at least one enzyme from the fermented by-product or residue, wherein the filamentous fungus may be selected from the group consisting of *Rhizopus, Aspergillus, Trichoderma*, and any combination thereof.

the by-product or residue can be a fibrous by-product selected from the group consisting of spent brewer's grains, dried distiller's grains, dried distiller's soluble, distiller's dried grains with soluble, wet grains, and mixtures thereof.

What is claimed is:

1. A method to improve the quality of by-products or residues derived from starch-containing material in a process for producing fermentation products comprising the steps of: i) adding an enzyme composition comprising an enzyme or a mixture of enzymes capable of degrading one or more fermented mash components to the fermented mash after fermentation to degrade the fermentation product, and ii) separating the desired distilling the degraded fermentation product.

2. The method according to claim 1, wherein the enzyme composition comprises an enzyme selected from the group consisting of an amylase, alpha-amylase, glucoamylase, a cellulase, a beta-glucanase, a hemicellulase, a xylanase, a pectinase, a mannanase, a protease, and a mixture thereof.

3. The method according to claim 1, wherein the enzyme composition comprises a beta-1,3-glucanase.

4. A method to improve the quality of by-products or residues derived from starch-containing material in a processes for producing fermentation products comprising the steps of: i) adding an enzyme composition comprising an enzyme or a mixture of enzymes capable of degrading one or more fermented mash components to the fermented mash after fermentation, wherein the enzyme composition comprises a beta-1,3-glucanase and a 1,6-beta-glucanase; and ii) separating the desired fermentation product.

5. The method according to claim 1, wherein the enzyme composition comprises a xylanase.

6. The method according to claim 1, wherein the enzyme composition comprises a beta-1,3-glucanase and a xylanase.

7. The method according to claim 1, wherein the enzyme composition comprises a beta-1,3-glucanase, a 1,6-beta-glucanase and a xylanase.

8. The method according to claim 1, wherein the enzyme composition comprises a beta-1,3-glucanase, a xylanase and a pectinase.

9. The method according to claim 1, wherein the enzyme composition comprises a beta-1,3-glucanase, a xylanase and a protease.

10. The method according to claim 1, wherein the enzyme composition comprises a mannanase.

11. The method according to claim 1, wherein the enzyme composition comprises a mannanase and a beta-1,3-glucanase.

12. The method according to claim 1, wherein the fermentation product is selected from the group consisting of an acid, an alcohol and hydrogen.

13. The method according to claim 12, wherein the alcohol is selected from the group consisting of ethanol, butanol, propanol, methanol, propanediol and butanediol.

14. The method according to claim 1, wherein the fermented mash is derived from a process of producing a fermentation product utilizing sugar-containing material as feedstock.

15. The method according to claim 1, wherein the fermented mash is derived from a process of producing a fermentation product utilizing starch-containing material as feedstock.

16. The method according to claim 1, wherein the feedstock is a cereal feedstock.

17. The method according to claim 1, wherein the by-product or residue is a fibrous by-product selected from the group consisting of spent brewer's grains, dried distiller's grains, dried distiller's soluble, distiller's dried grains with soluble, wet grains, and mixtures thereof.

18. The method according to claim 1, wherein the fermented mash is derived from a process of producing a fermentation product utilizing whole grain obtained from cereals as feedstock, the fermentation product is ethanol, the ethanol is separated by distillation and the improved by-product is Dried Distillers Grains with Solubles (DDGS).

19. The method according to claim 1, wherein by-products or residues have an improved nutrition quality and are used in animal feed.

20. A method of producing ethanol from starch containing material, said method comprising the steps of:
    i) Converting starch containing material to fermentable sugars;
    ii) Fermentation of the fermentable sugars with a microorganism to fermented mash;
    iii) Adding an enzyme composition comprising an enzyme or a mixture of enzymes to the fermented mash after fermentation to degrade the fermentation product; and
    iv) Separation of the ethanol in the fermented mash degraded fermentation product by distillation.

21. The method according to claim 20, wherein the enzyme composition comprises an enzyme selected from the group consisting of an amylase, an alpha-amylase, a glucoamylase, a cellulase, a beta-glucanase, a hemicellulase, a xylanase, a pectinase, a mannanase, a protease, and a mixture thereof.

22. The method according to claim 20, wherein the enzyme composition comprises a beta-1,3-glucanase.

23. The method according to claim 20, wherein the enzyme composition comprises a xylanase.

24. The method according to claim 20, wherein the enzyme composition comprises a beta-1,3-glucanase and a xylanase.

25. The method according to claim 20, wherein the enzyme composition comprises a beta-1,3-glucanase, a xylanase and a pectinase.

26. The method according to claim 20, wherein the enzyme composition comprises a beta-1,3-glucanase, a xylanase and a protease.

27. The method according to claim 20, wherein the enzyme composition comprises a mannanase.

28. The method according to claim 20, wherein the enzyme composition comprises a mannanase and a beta-1,3-glucanase.

29. The method according to claim 20, wherein the starch containing material is obtained from cereals and/or tubers.

30. The method according to claim 20, wherein the by-product or residue is a fibrous by-product selected from the group consisting of spent brewer's grains, dried distiller's grains, dried distiller's soluble, distiller's dried grains with soluble, wet grains, and mixtures thereof.

* * * * *